US008382799B2

(12) United States Patent
Trenhaile

(10) Patent No.: US 8,382,799 B2
(45) Date of Patent: Feb. 26, 2013

(54) VARIABLE TENSION POST FIXATION

(75) Inventor: Scott Trenhaile, Belvidere, IL (US)

(73) Assignee: Rockford Orthopaedic Sports Medicine Services, LLC, Belvidere, IL (US)

( * ) Notice: Subject to any disclaimer, the term of this patent is extended or adjusted under 35 U.S.C. 154(b) by 562 days.

(21) Appl. No.: 12/578,324

(22) Filed: Oct. 13, 2009

(65) Prior Publication Data

US 2010/0100127 A1 Apr. 22, 2010

Related U.S. Application Data

(60) Provisional application No. 61/104,881, filed on Oct. 13, 2008.

(51) Int. Cl.
*A61B 17/04* (2006.01)
(52) U.S. Cl. .................................................. 606/232
(58) Field of Classification Search .............. 606/139, 606/151, 232
See application file for complete search history.

(56) References Cited

U.S. PATENT DOCUMENTS

| 5,207,679 | A | * | 5/1993 | Li ................................. 606/232 |
| 5,234,430 | A | | 8/1993 | Huebner |
| 5,364,400 | A | | 11/1994 | Rego, Jr. et al. |
| 5,456,685 | A | | 10/1995 | Huebner |
| 5,584,835 | A | * | 12/1996 | Greenfield .................... 606/232 |
| 5,707,395 | A | | 1/1998 | Li |
| 5,849,004 | A | * | 12/1998 | Bramlet ........................ 606/232 |
| 5,902,321 | A | * | 5/1999 | Caspari et al. ............... 606/232 |
| 6,001,106 | A | | 12/1999 | Ryan et al. |
| 6,045,554 | A | | 4/2000 | Grooms et al. |
| 6,562,071 | B2 | | 5/2003 | Jarvinen |
| 6,666,877 | B2 | * | 12/2003 | Morgan et al. ............... 606/232 |
| 7,081,126 | B2 | | 7/2006 | McDevitt et al. |
| 2008/0058819 | A1 | | 3/2008 | Wolf |

OTHER PUBLICATIONS

Non-Final Office Action mailed Mar. 28, 2012 for U.S. Appl. No. 12/578,327, 9 pages.
Final Office Action for U.S. Appl. No. 12/578,327 mailed Oct. 10, 2012, 14 pgs.

* cited by examiner

*Primary Examiner* — Gregory Anderson
(74) *Attorney, Agent, or Firm* — Dicke, Billig & Czaja, PLLC

(57) ABSTRACT

A variable tension post fixation device includes an outer body including a shaft, a tip, and a central core, and an inner body including a suture hole and configured to be advanceable within the central core, wherein the outer body is configured for allowing insertion of the outer body into a pilot hole in a bone, and wherein the outer body and inner body cooperate to secure sutures in the bone.

18 Claims, 27 Drawing Sheets

VARIABLE TENSION POST FIXATION

CROSS REFERENCE TO RELATED APPLICATIONS

This application claims priority under 35 U.S.C. §119(e) to U.S. Provisional Patent Application Ser. No. 61/104,881 filed on Oct. 13, 2008, and incorporated herein by reference. This application is related to U.S. Non-Provisional patent application Ser. No. 12/578,327, filed on even date herewith, and incorporated herein by reference.

FIELD OF THE INVENTION

The present invention relates generally to a medical device that facilitates orthopaedic procedures requiring tensioning and fixation of sutures to bone. With this device, variable tension may be applied independently to one or more different sets of sutures. For example, during anterior cruciate ligament (ACL) reconstruction, the device may be used as primary or secondary fixation of an ACL graft on the tibial side of the reconstruction construct. With the device, variable tension may be applied independently to the sutures, such as those found with single or double bundle ACL reconstruction.

BACKGROUND OF THE INVENTION

Anterior cruciate ligament (ACL) reconstruction is one of the most commonly performed procedures on the human knee. Primary surgical goals during ACL reconstruction include restoring translational and rotational stability of the knee. These goals are often achieved by utilizing a soft tissue graft that is fixated on the femoral and tibial sides of the joint. A common cause of graft failure within the first 6 weeks is loss of fixation strength. This loss of fixation strength is more commonly found on the tibial side rather than the femoral attachment of the ACL graft.

To alleviate the loss of fixation strength, surgeons often use a screw and washer on the tibial side of the joint to create a backup fixation whereby the suture tails of the ACL graft are tied around the screw as a post. A simple limitation with this type of backup fixation, however, is that the sutures tied around the screw can not be tensioned once they are tied. Furthermore, with the advent of double bundle ACL reconstruction, a need for independent tensioning of each ACL bundle has evolved. Unfortunately, the simple screw and washer configuration does not allow for independent tensioning of the four suture tails on the two independent bundle limbs.

The ability to attach sutures around a post and then be able to further tension those sutures to a desired tension after they have been tied would be beneficial, for example, during ACL reconstruction. Also, a desirable device would allow for independent tensioning of two sets of suture tails on a single tibial post, including tensioning of suture tails often found on the tibial side of the joint when performing a double bundle ACL graft.

For these and other reasons, there is a need for the present invention.

BRIEF DESCRIPTION OF THE DRAWINGS

FIGS. 2a through 2g illustrate an embodiment of a variable tension post fixation device.

DETAILED DESCRIPTION

A desirable fixation device would provide orthopaedic surgeons performing single or double bundle ACL reconstruction with the ability to tension suture tails after the suture tails are attached to the fixation device. The device would allow the surgeon to tension each strand of the suture tails to a desired tension, and then tension the entire construct one last time in a combined fashion if desired.

Techniques

Figure 5:
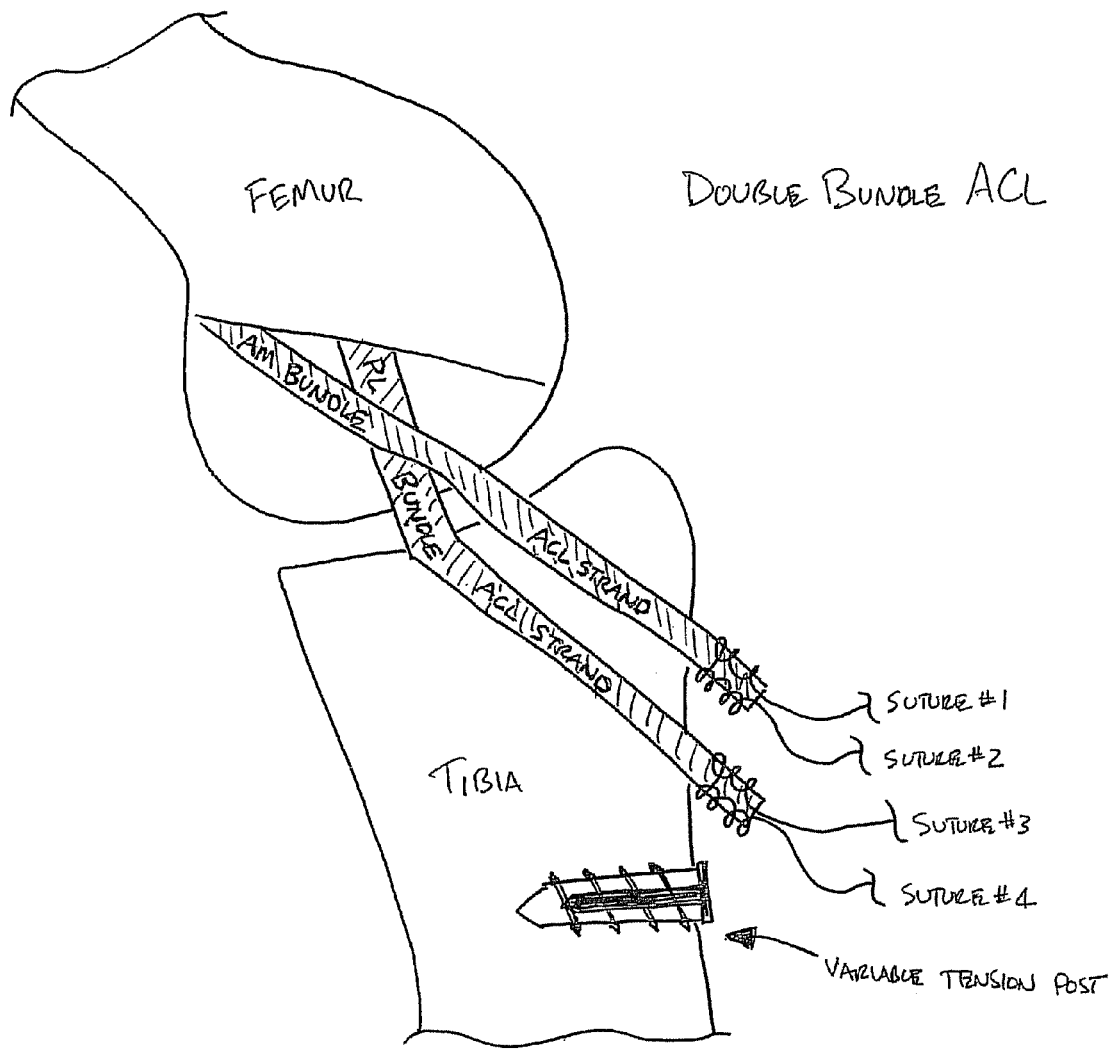
FIG. 5 illustrates one technique of performing ACL reconstruction using a variable tension post fixation device as described herein.

With reference to FIG. 5, one technique of performing single or double bundle ACL reconstruction is described. The tunnels are drilled, the graft(s) are passed through their respective tunnels, and the femoral fixation is placed. In double bundle reconstruction, each bundle is pulled out of their respective tibial tunnel. For fixation of each bundle, the surgeon may use interference screws in each tunnel as a primary fixation. Secondary fixation may include variable tensioning with separate fixation devices, as described herein, positioned distal to the exit of each tibial tunnel or may include combining the four strands of the sutures from the two bundles of the double bundle ACL and providing variable tensioning with a single fixation device, as described herein. The disclosed fixation device would allow each ACL bundle (2 suture tails per bundle) to be variably tensioned independent of the other on a single post.

Although the disclosed fixation device is described for use in performing single or double bundle ACL reconstruction, it is understood and within the scope of the present invention for the disclosed fixation device to be used in other procedures where tensioning of sutures is desired.

Variable Tension Posts

FIGS. 1a through 1i illustrate one embodiment of a variable tension post fixation device. The variable tension post fixation device of FIGS. 1a through 1f includes an outer screw (or sleeve) and an inner key configured to fit within the outer screw (or sleeve). The outer screw and inner key cooperate to provide for variable tension fixation of sutures, as described below.

In one embodiment of use, a drill guide is placed distal to the exit point of the most distal tibial tunnel, and a pilot hole is drilled in the bone (see FIG. 5). After the pilot hole is drilled, the outer screw of the variable tension post fixation device is placed in the pilot hole.

Figure 1A:
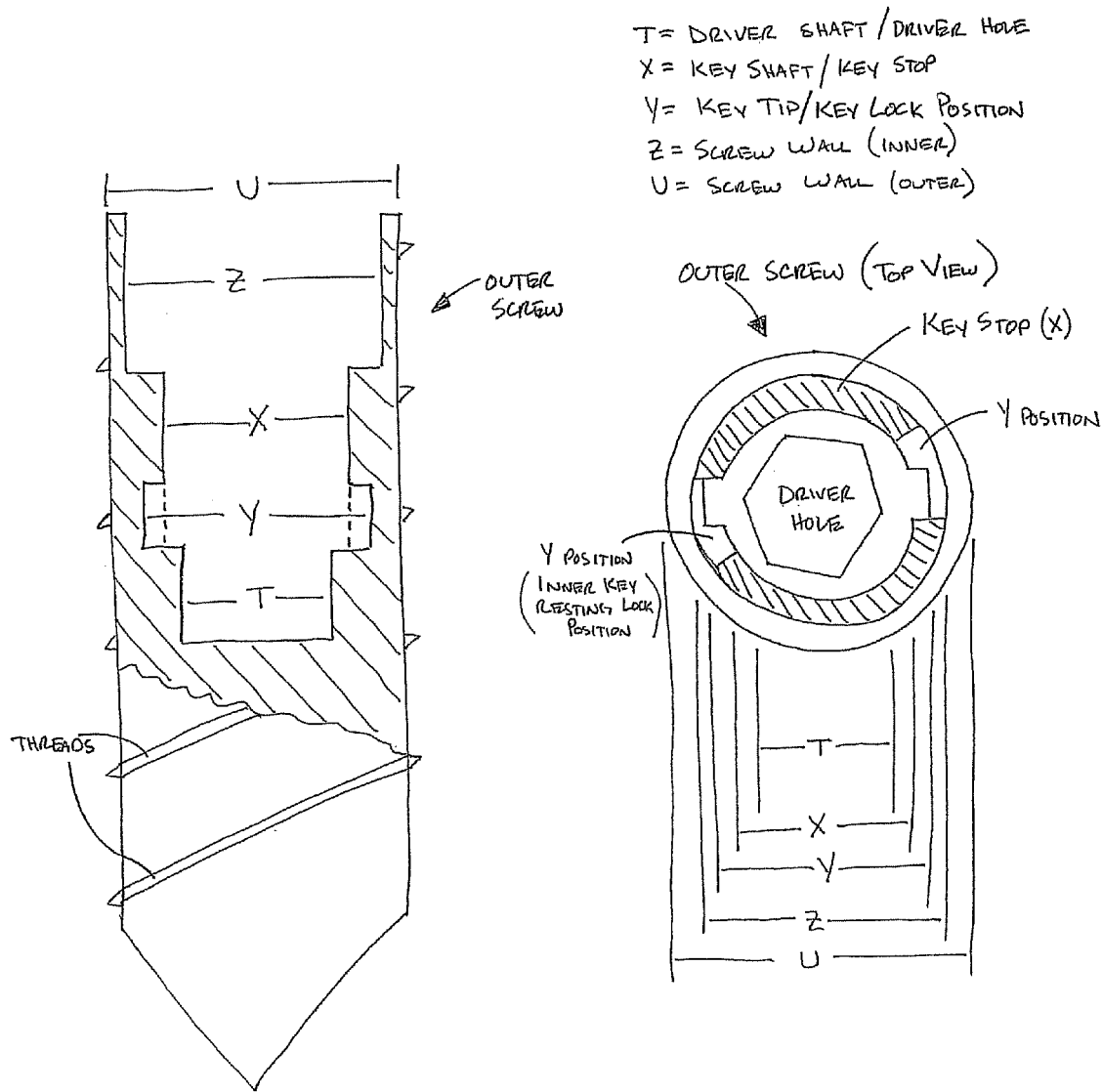
FIGS. 1a through 1i illustrate an embodiment of a variable tension post fixation device.
Figure 1B:
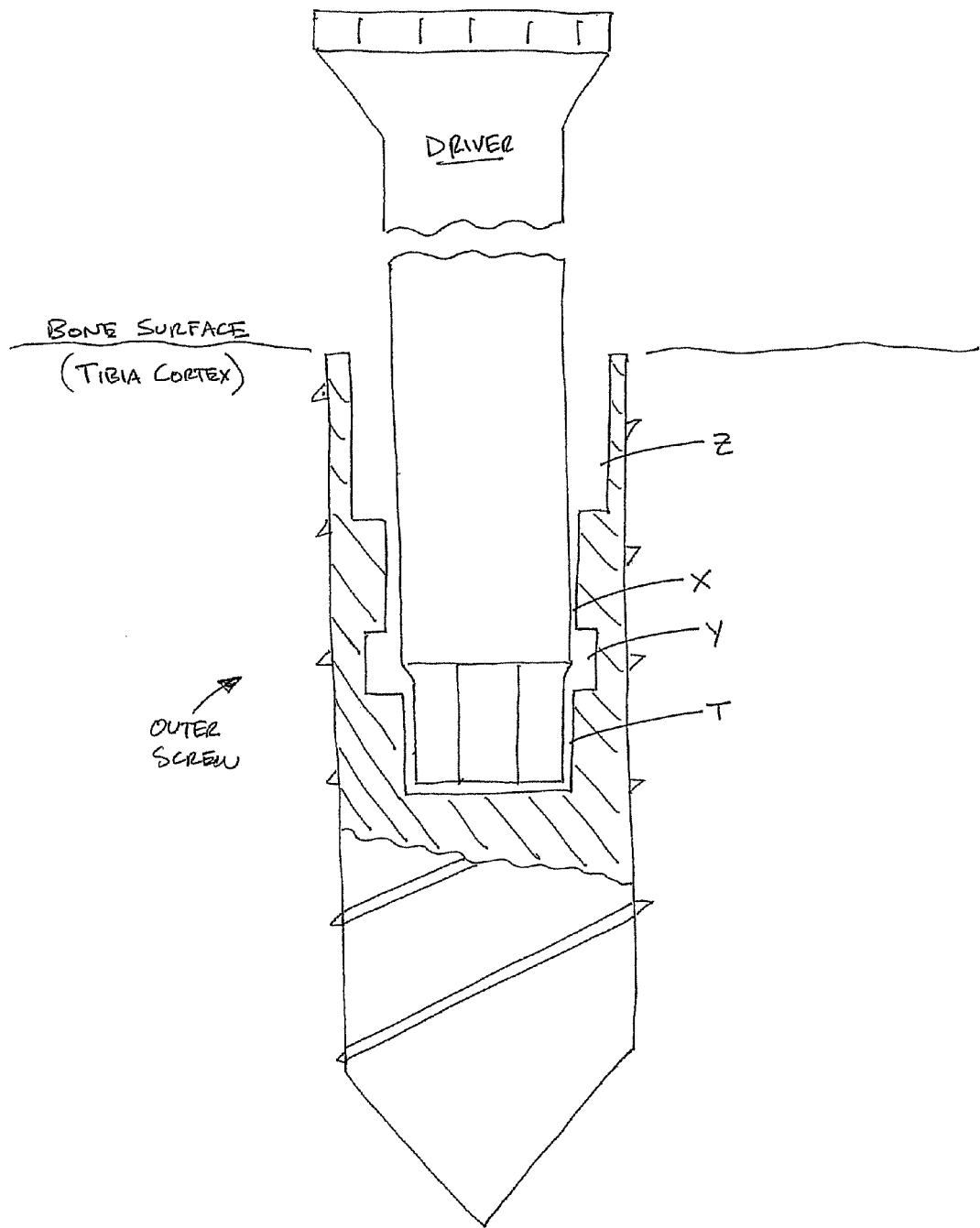
Figure 1C:
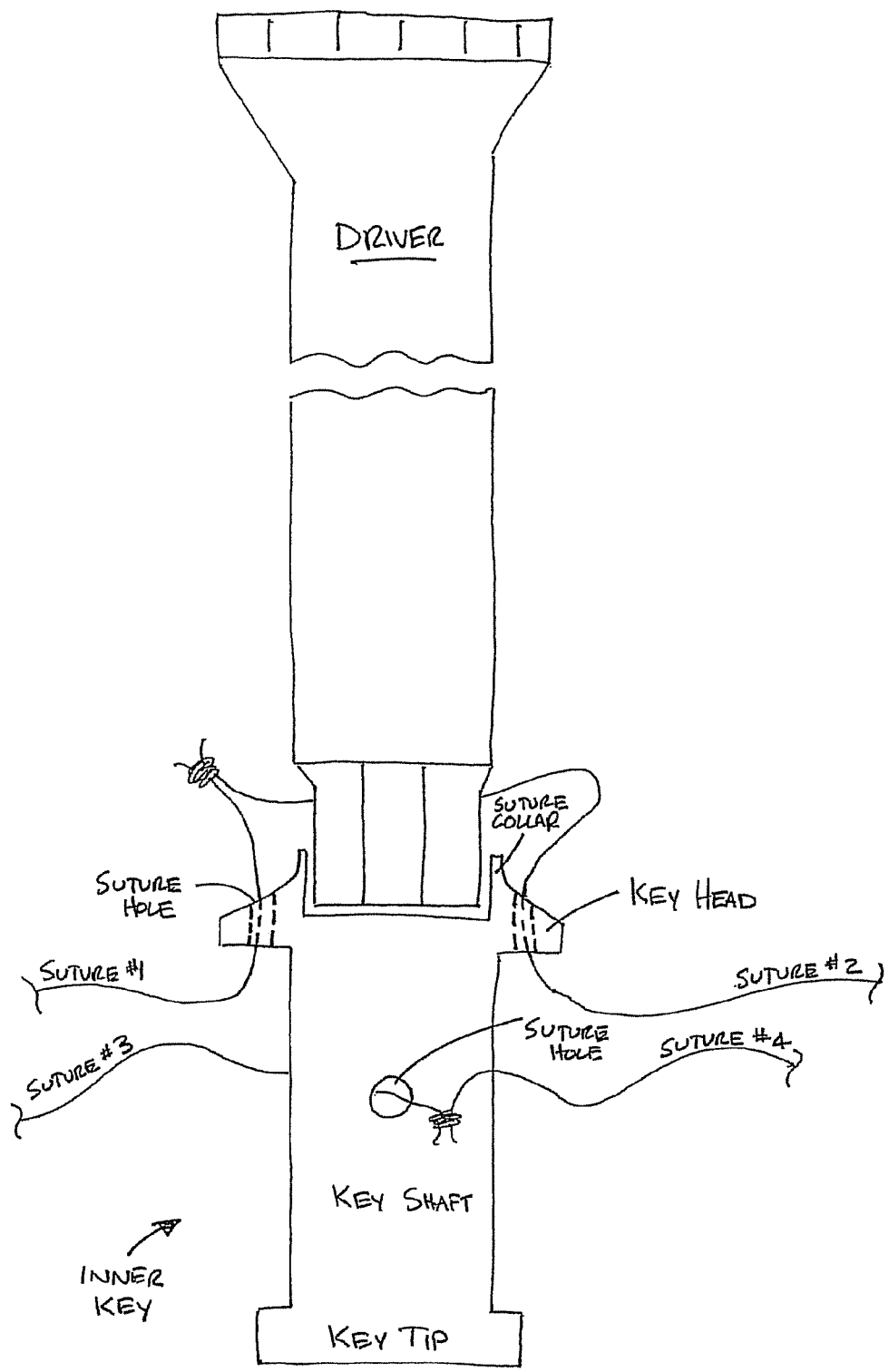
Figure 1D:
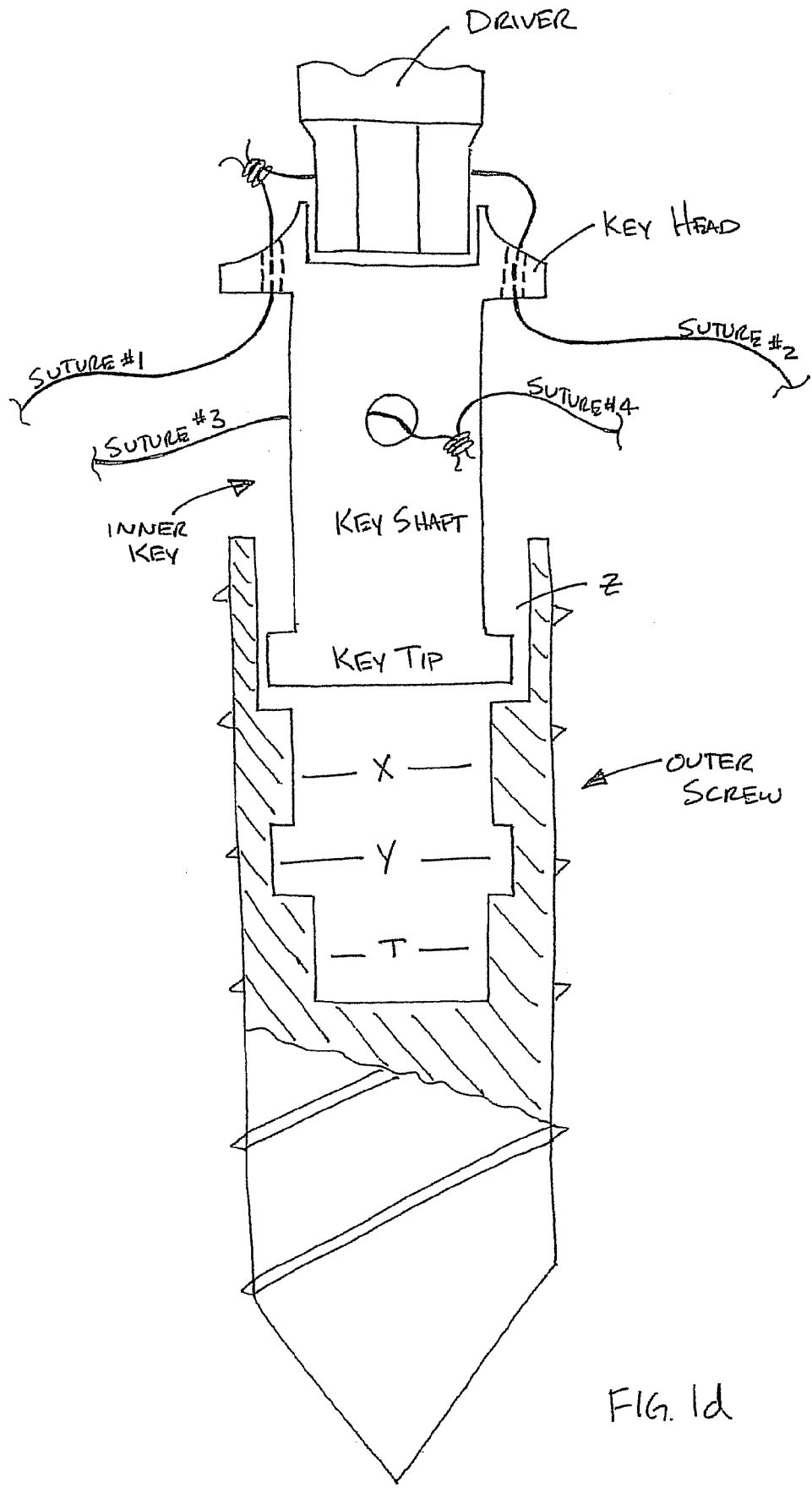
Figure 1E:
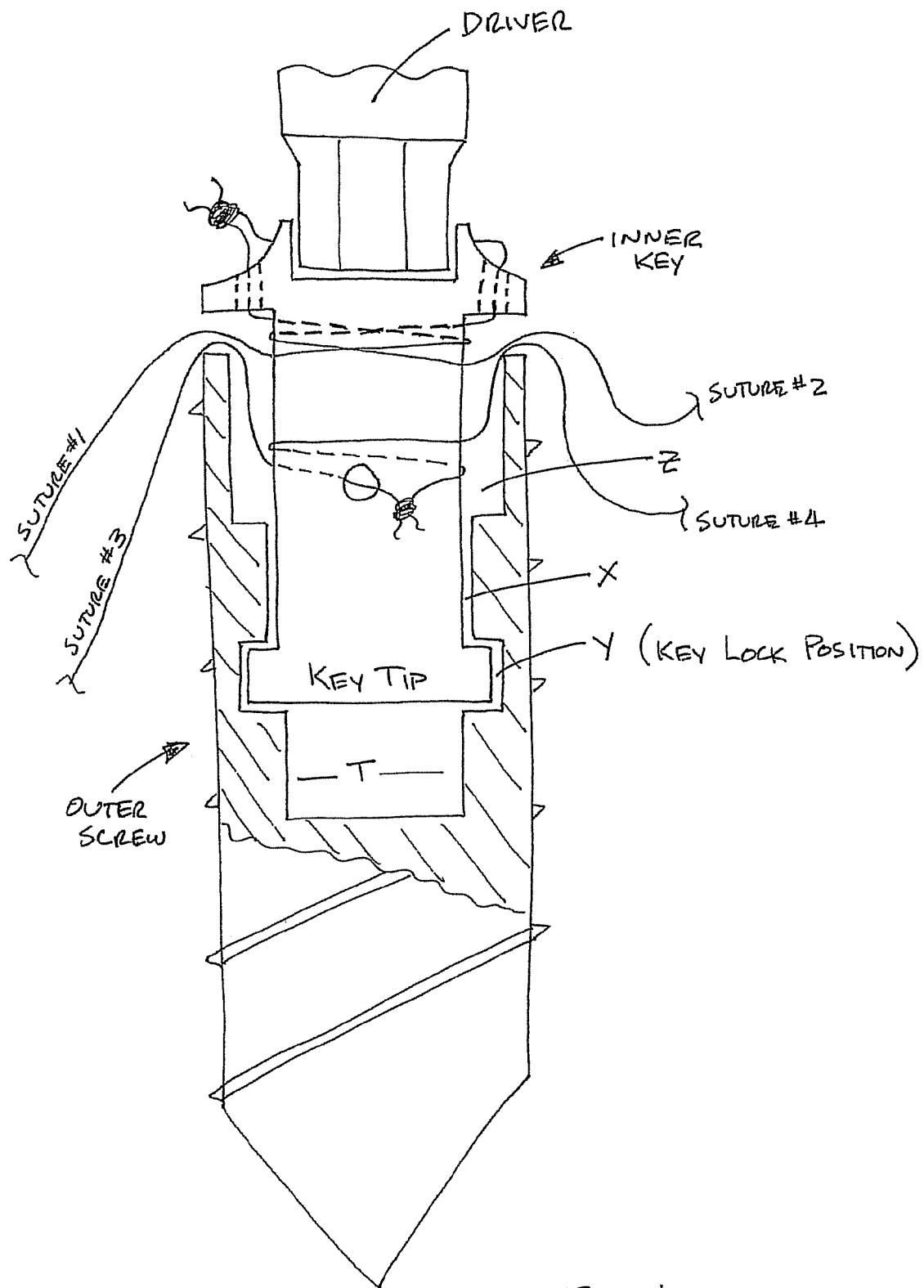

In one embodiment, the outer screw is fully threaded and headless, and includes a series of concentric channels or bores (t, x, y, z) (FIG. 1a). In one embodiment, the outer screw is inserted nearly flush with the cortex of the bone (FIG. 1b), and provides a recipient sight for the inner key (see FIGS. 1d, 1e). In one embodiment, the inner key includes a key tip, a key shaft, and a key head, with the key head being approximately the same diameter as the outer screw (FIG. 1c, 1d, 1e).

The concentric bores or channels of the outer screw allow for insertion of the outer screw into the pilot hole in the bone, and locking of the inner key within the outer screw. In one embodiment, the outer screw is secured in the pilot hole with a driver by engaging the driver in the channel or bore t (FIG.

1b). After the outer screw is anchored in the bone, the driver is removed and the suture tails are fed through and/or attached to the inner key (FIG. 1c).

Figure 1F:
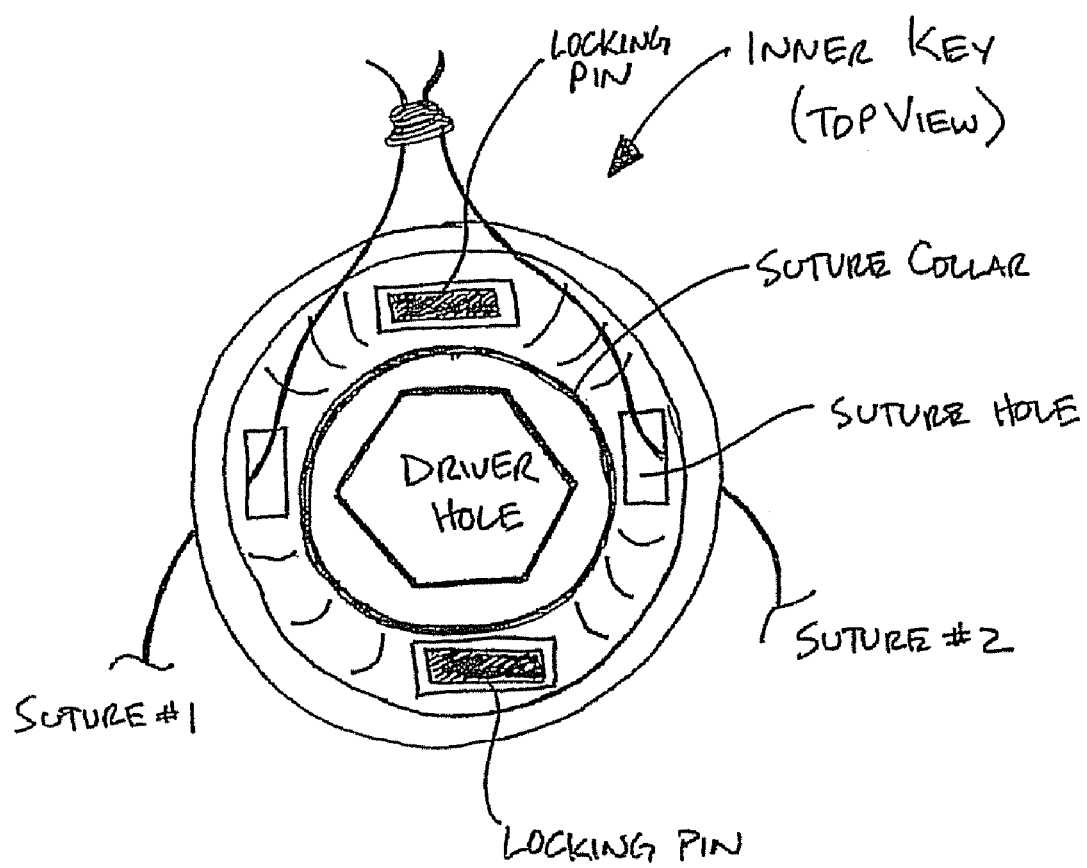

In one embodiment, the key head of the inner key has 2 holes through which sutures are fed. In one embodiment, suture tails 1 and 2 are fed through the key head from the bottom up and then tied to each other (FIGS. 1c, 1f). This helps to keep the twisted sutures under the key head and around the key shaft. In one embodiment, suture tails 3 and 4 are fed through a central hole in the key shaft and tied to each other (FIG. 1c). The key tip is then inserted into the outer screw channel or bore z, and the inner key is rotated in order to tension the sutures (FIG. 1d). In one embodiment, the inner key is rotated using the same size driver used for the outer screw. In one embodiment, a collar is provided around the key head to help prevent the suture tails 1 and 2 from slipping onto the driver during rotation of the inner key.

Once the desired tension on the sutures has been obtained, the driver is used to rotate the inner key and advance the key tip through the channel or bore x until the key tip reaches the channel or bore y (FIG. 1e). In one embodiment, the sutures are slightly over-tensioned as the key tip is advanced through the channel or bore x and into the locking channel or bore y. Slightly over tensioning the sutures will allow for the inner key to "unwind" within the locking channel or bore y, as the key tip rotates to the lock position (FIG. 1a).

In one embodiment, locking pin slots are provided in the key head, and locking pins are inserted into the slots to prevent the inner key from rotating relative to the outer screw when the inner key is in the "locked" position (FIGS. 1e, 1f). In one embodiment, the locking pins extend along the key shaft through the key shaft channel or bore x and into the locking channel or bore y next to the key tip (FIGS. 1e, 1a). As such, the key tip of the inner key and, therefore, the inner key itself is prevented from rotating within the locking channel or bore y.

In one embodiment, if the ACL bundles need to be further tensioned, the entire construct (inner key and outer screw) can be advanced farther into the pilot hole by inserting the driver into the key head and turning the entire construct clockwise. Because the outer diameters of the outer screw and the inner key are essentially the same, the entire construct can be advanced as a unit even beyond the cortex of the tibial bone posteriorly.

Figure 1G:
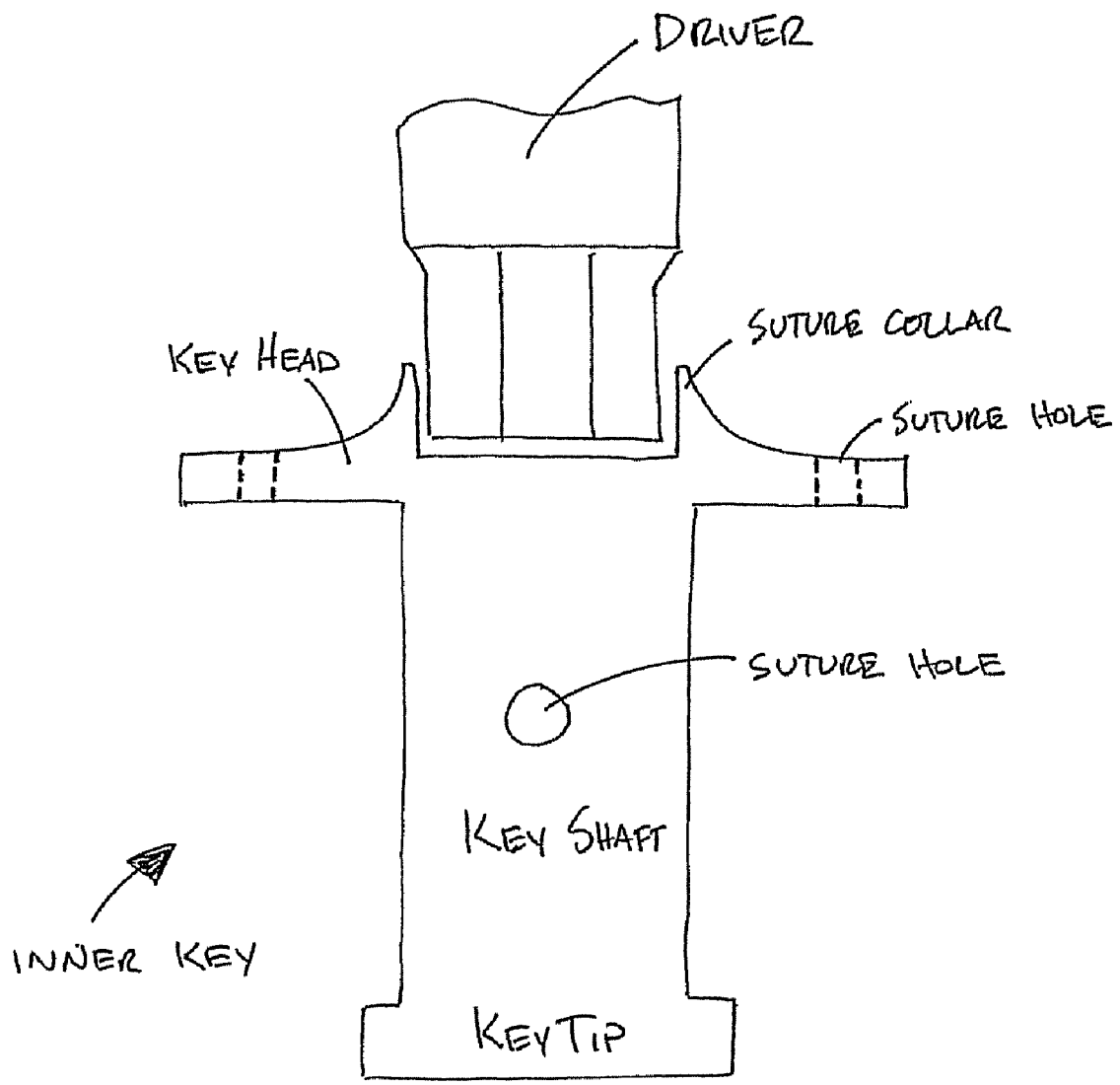
Figure 1H:
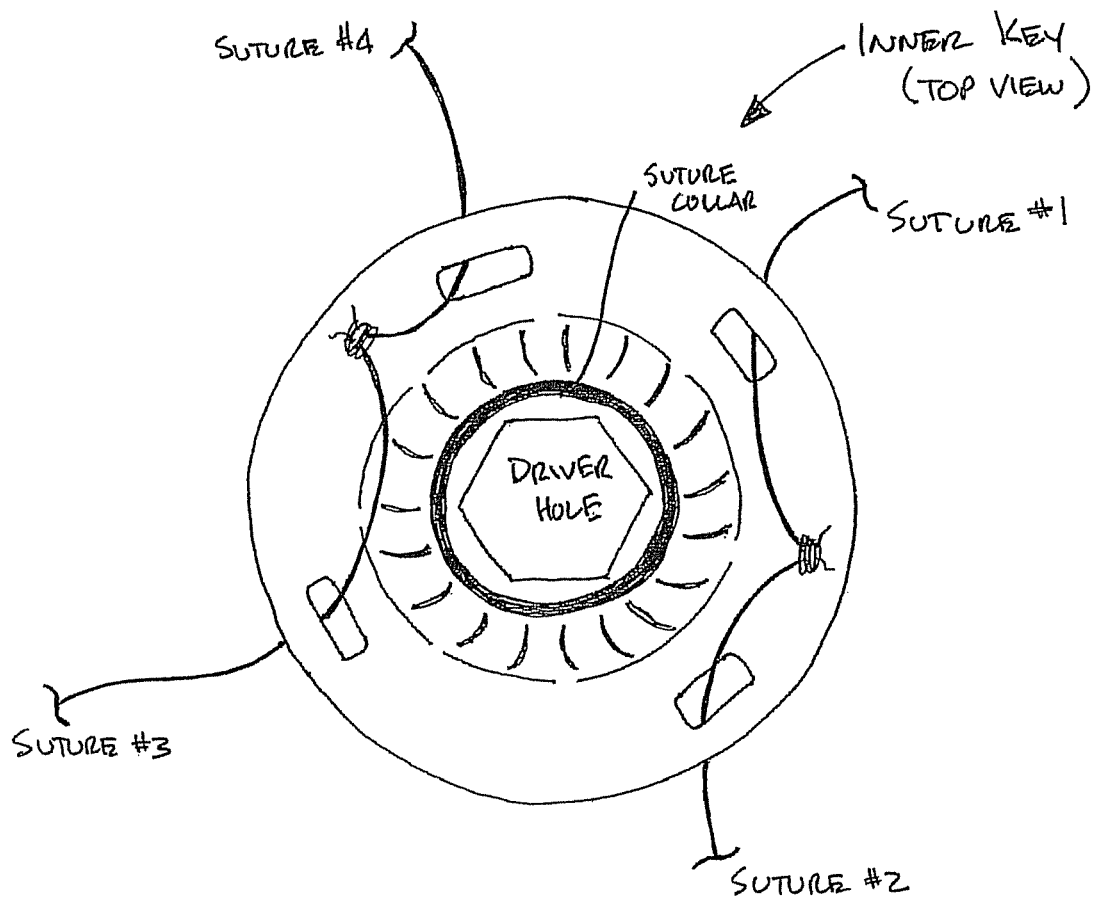
Figure 1I:
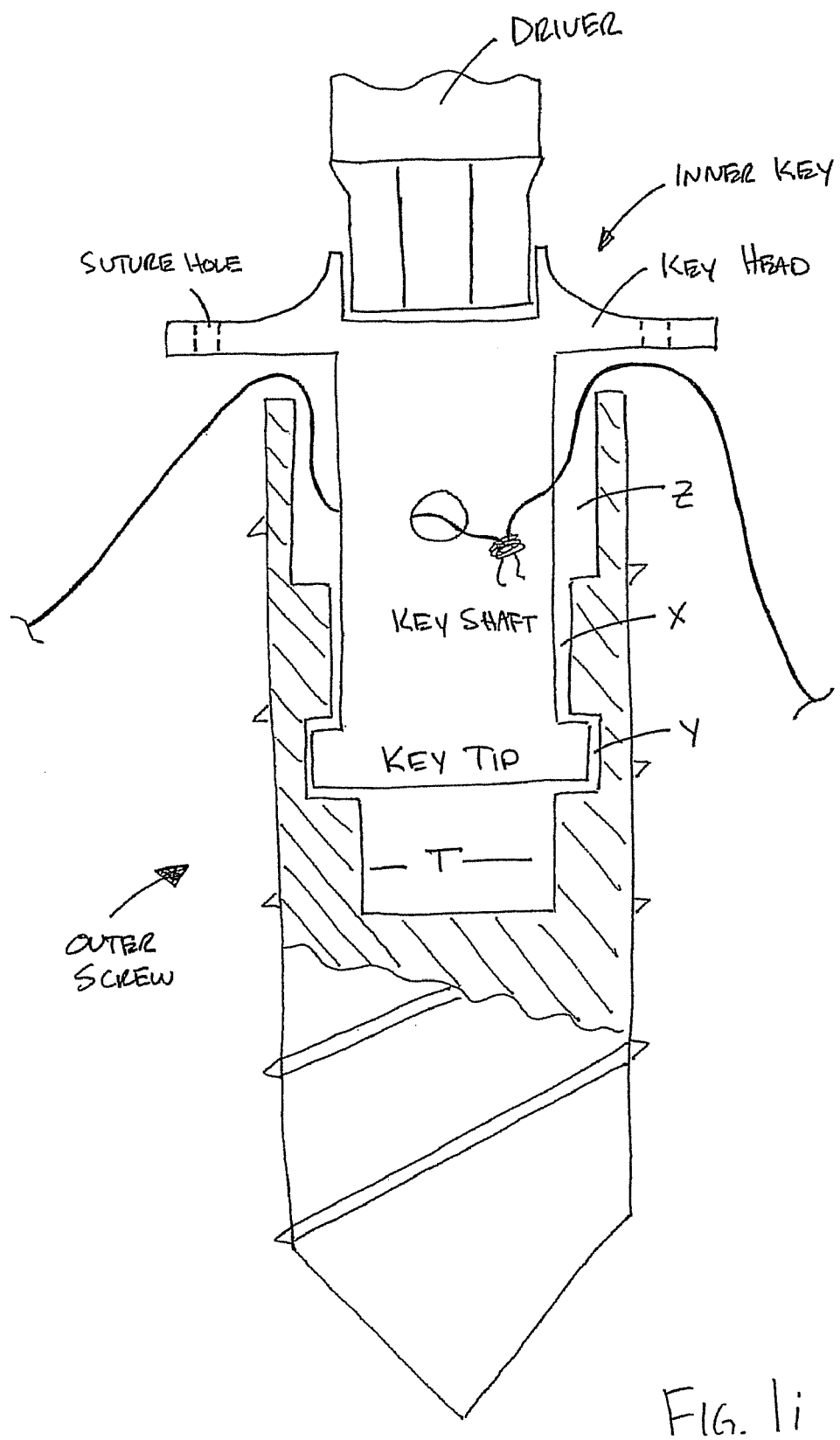

The variable tension post fixation device of FIGS. 1g through 1i is similar to the variable tension post fixation device of FIGS. 1a through 1f, however, the inner key of the variable tension post fixation device of FIGS. 1g through 1i has a larger diameter head than the outer screw (FIG. 1g, 1i). The larger diameter head provides more room to bring all four suture tails from the bottom up through their own hole (FIG. 1h). In one embodiment, suture tails 1 and 2 are fed up through the key head and tied to each other, as are suture tails 3 and 4. In one embodiment, as described above, a collar is provided around the key head to help keep the sutures from becoming entangled with the driver. In one embodiment, in addition to the holes for sutures in the key head, a central hole is provided in the key shaft for additional sutures (FIG. 1i).

The inner key of the variable tension post fixation device of FIGS. 1g through 1i is "locked" in the locking channel or bore y of the outer screw in a manner similar to that described above. In one embodiment, however, the key head of the inner screw is still spaced or offset from the top of the outer screw when the inner key is in the "locked" position (FIG. 1i). This slight offset allows for further advancement of the entire construct once the inner key is locked to the outer screw whereby further tensioning of the sutures at the conclusion of the procedure is possible.

Figure 2A:
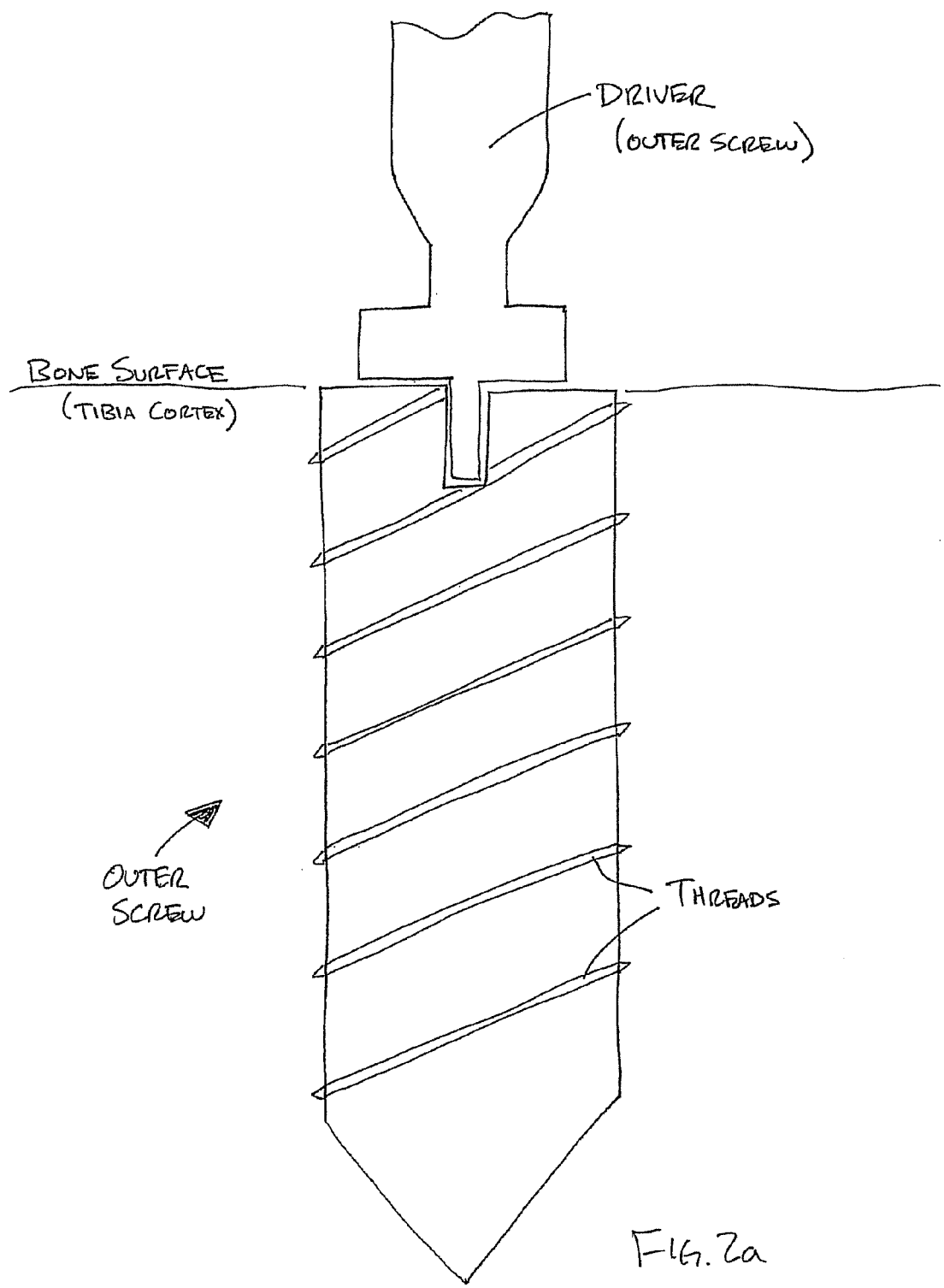
Figure 2B:
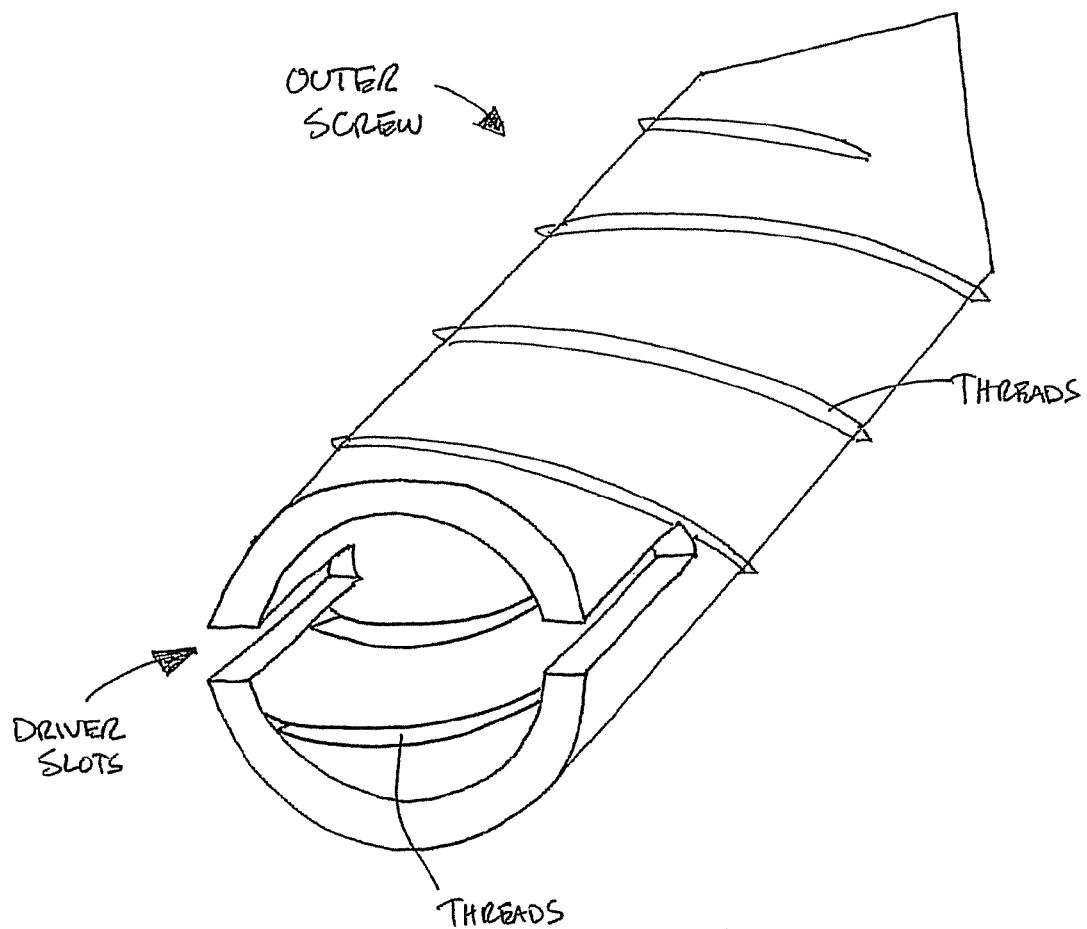
Figure 2C:
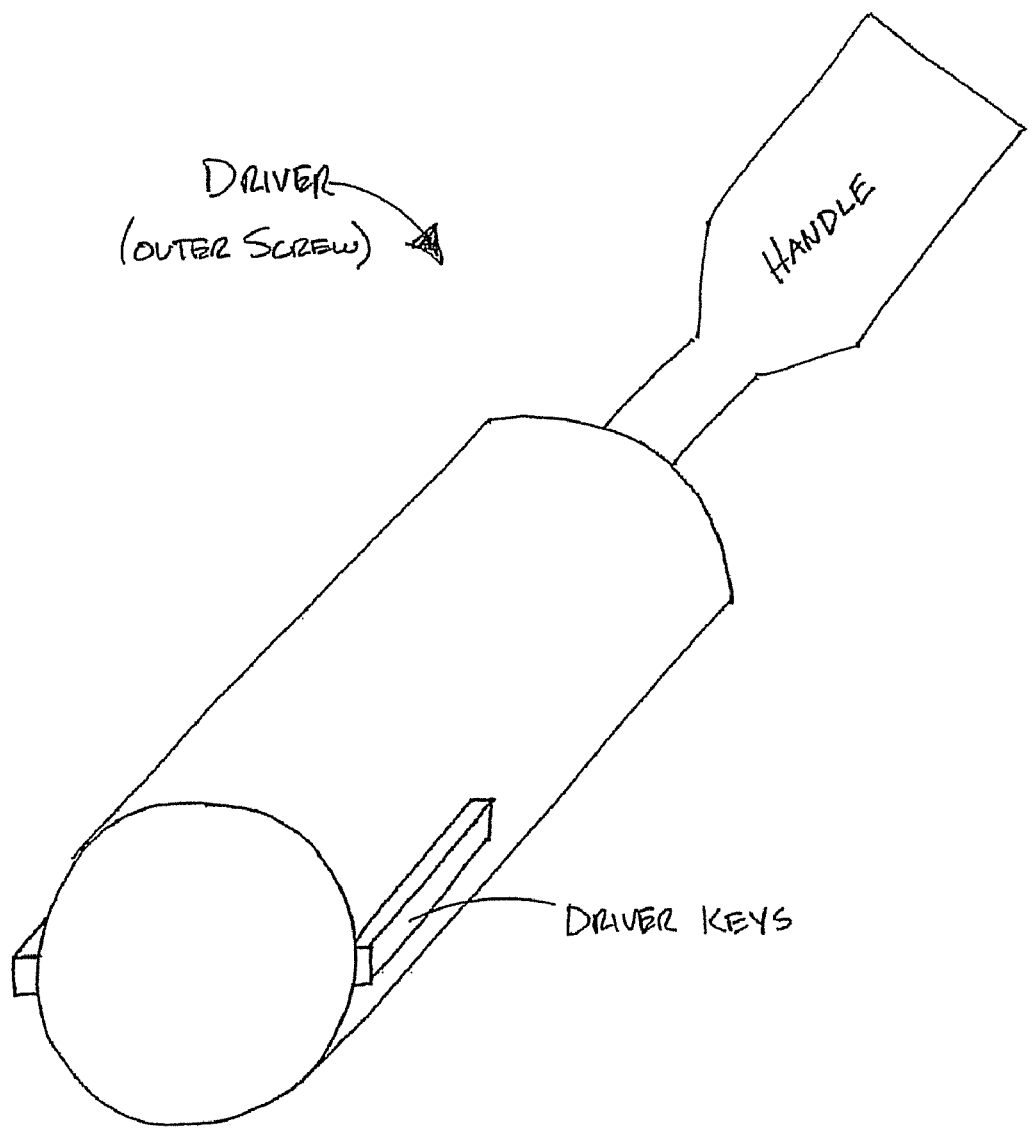

FIGS. 2a through 2g illustrate another embodiment of a variable tension post fixation device. In one embodiment, as outlined above, a drill is used to create a pilot hole in the tibia distal to the most distal exiting tibial ACL bundle (see FIG. 5). The variable tension post fixation device of FIGS. 2a through 2g includes an outer screw and an inner screw. In one embodiment, the outer screw is a fully threaded headless screw that is inserted flush to the cortex of the tibial bone (FIG. 2a). In one embodiment, the outer screw is incompletely cannulated and includes side channels that are cut partially along the sides to receive a driver (FIGS. 2a, 2b). In one embodiment, the driver is cylindrical and includes expansion keys or tabs that correspond to the side channels of the outer screw to provide ease of insertion and stability when anchoring the outer screw in the bone (FIG. 2c).

Figure 2D:
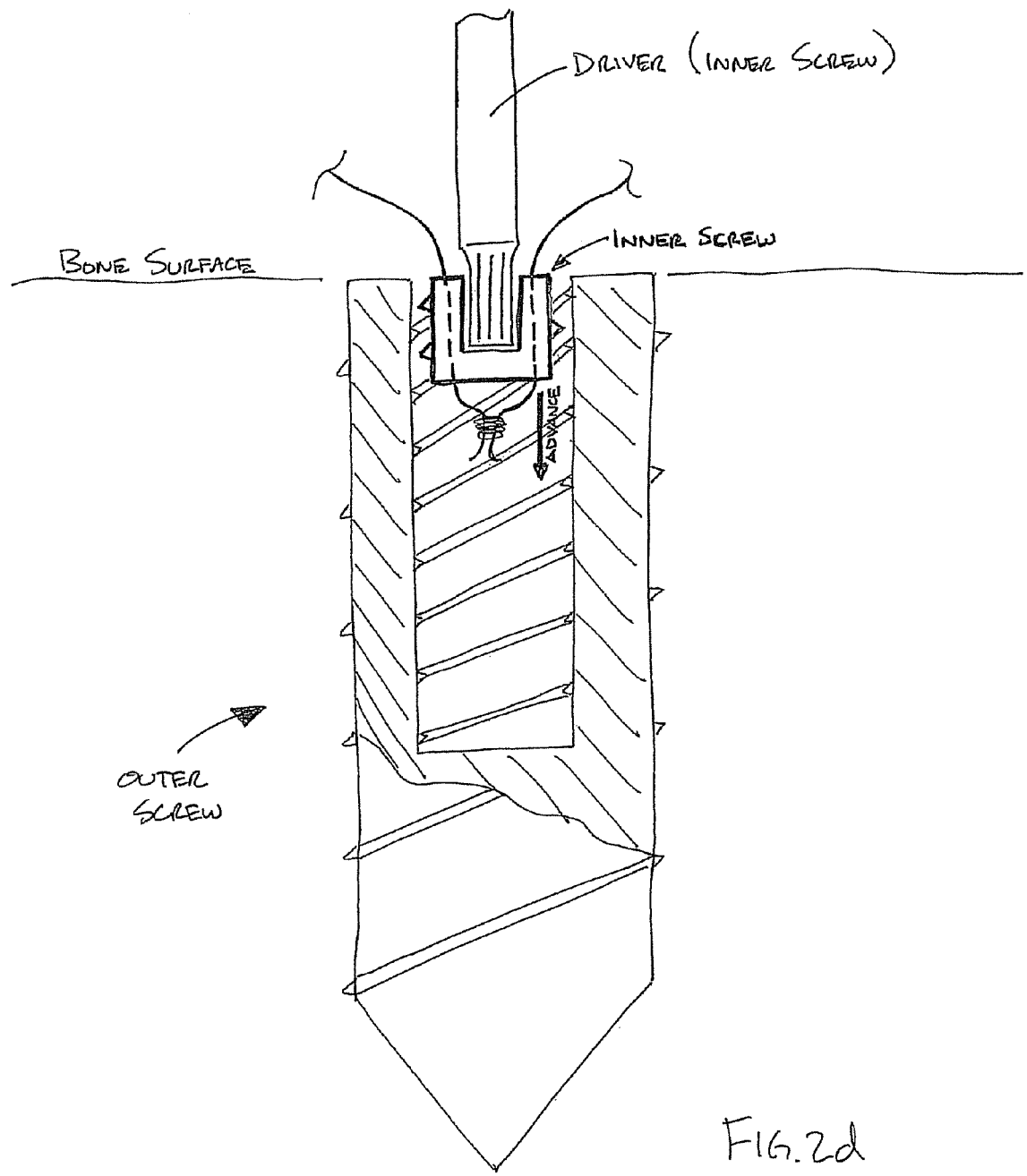
Figure 2C:
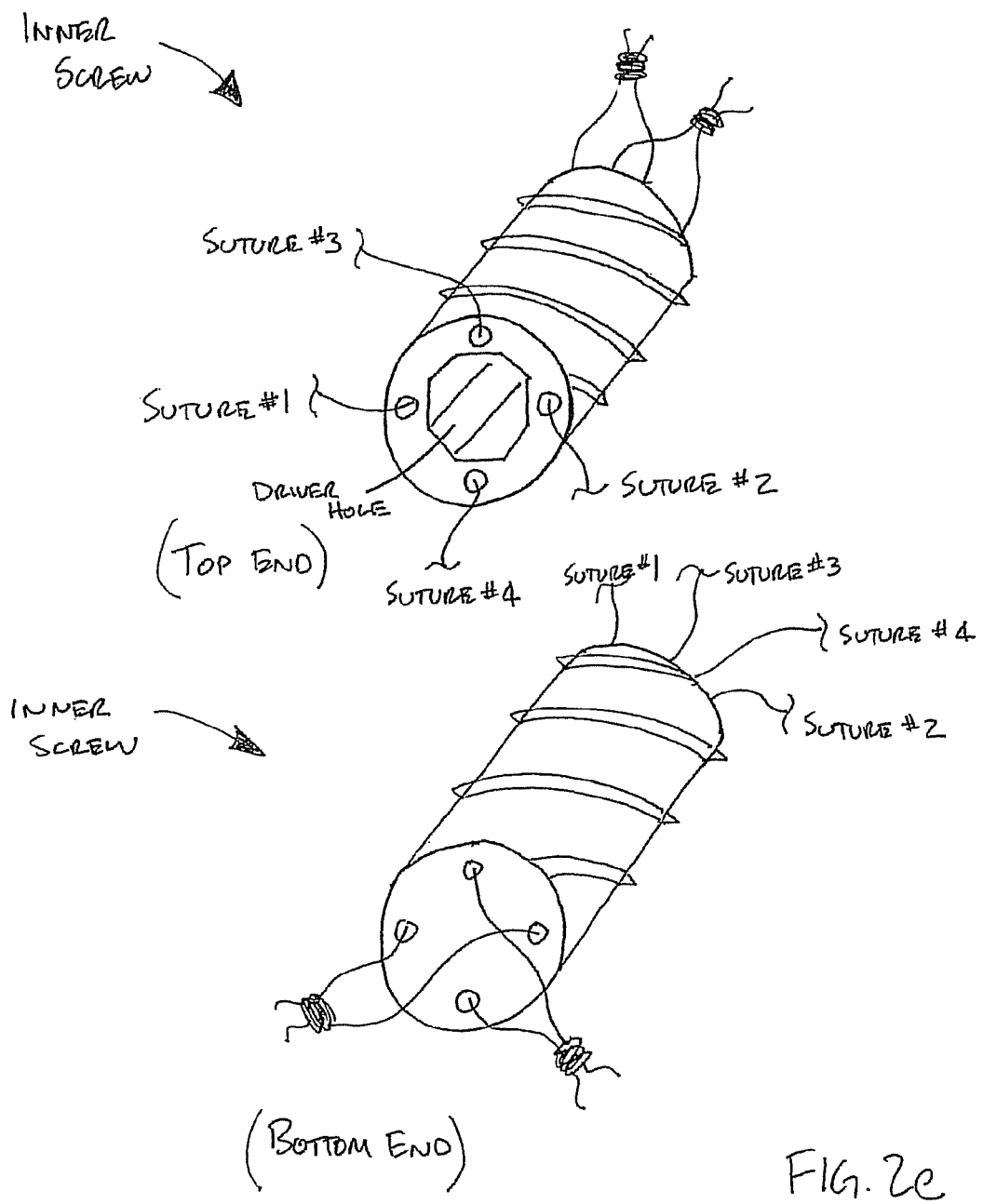

In one embodiment, the inner portion of the outer screw of the variable tension post fixation device of FIGS. 2a through 2g has threads that extend to the bottom of the cannulation portion of the screw (FIG. 2d). In addition, the inner screw is threaded and also partially cannulated to receive a driver (FIGS. 2d, 2e). In one embodiment, the inner screw has 4 holes formed axially therethrough to accommodate sutures (FIG. 2e). In one embodiment, suture tails 1 and 2 are each fed through respective holes in the inner screw and tied to each other, as are suture tails 3 and 4 (FIG. 2e). The inner screw is then placed into the threaded cannulation of the outer screw and advanced with the driver until the desired tension is achieved on the sutures (FIG. 2d).

Figure 2F:
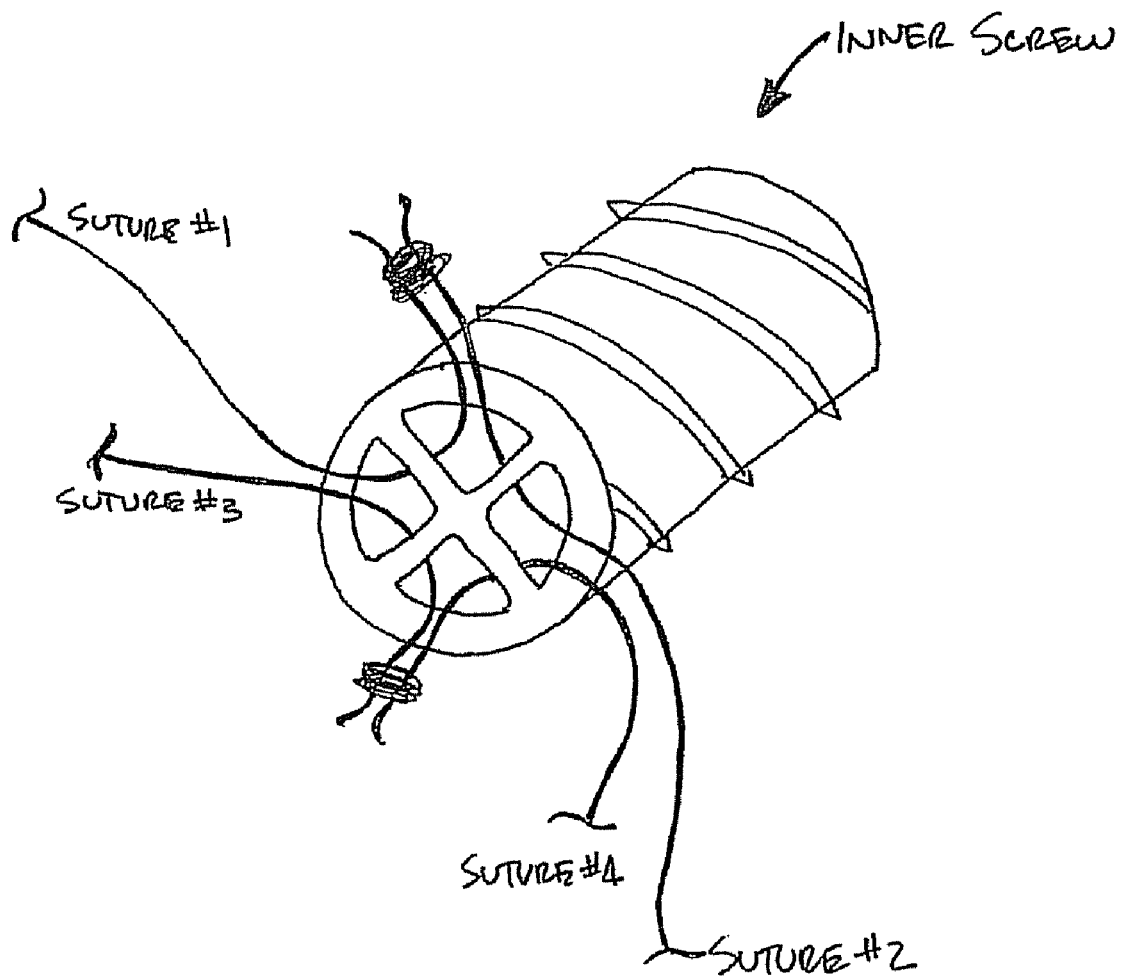
Figure 2G:
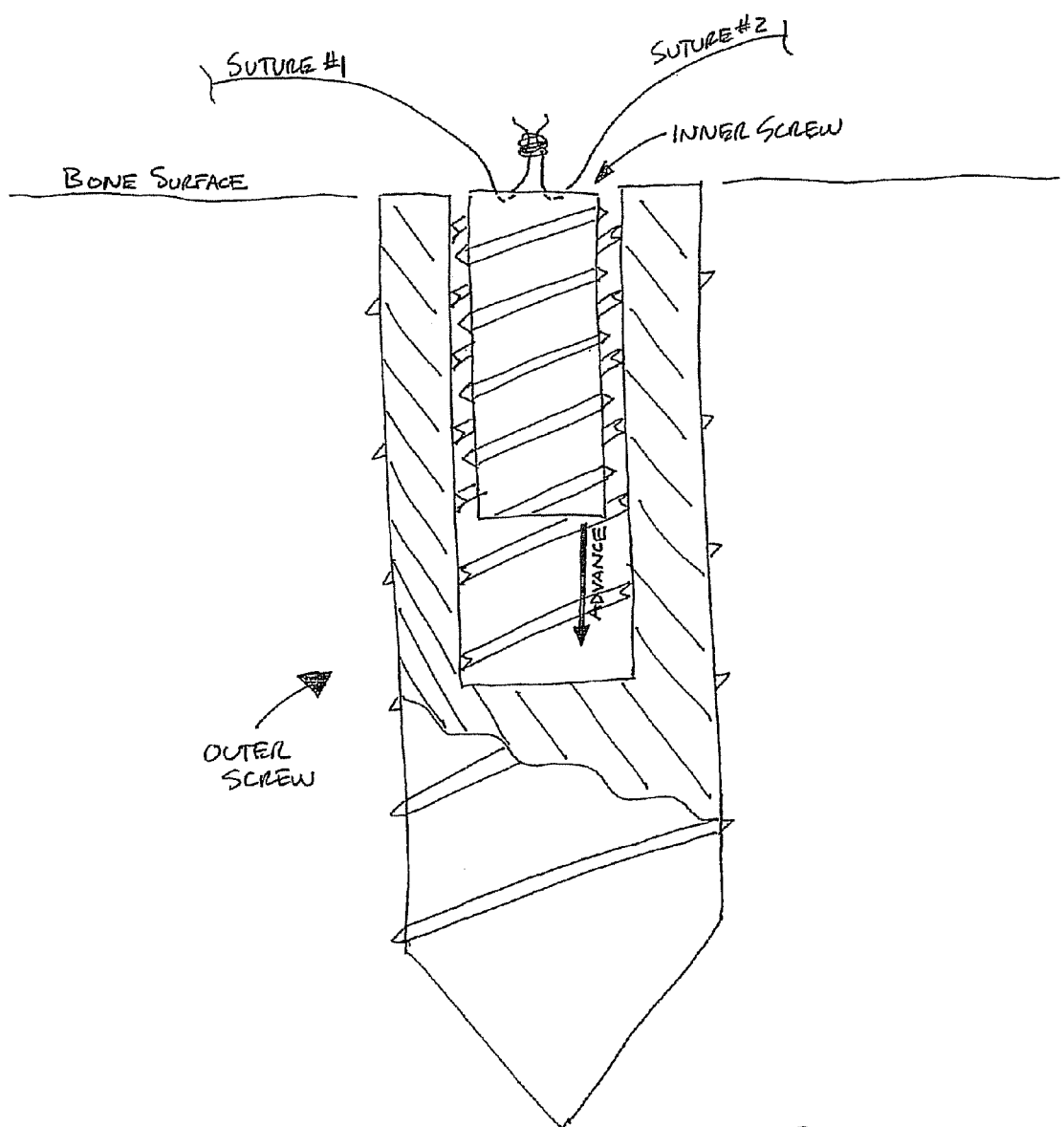

The variable tension post fixation device of FIGS. 2f through 2g is similar to the variable tension post fixation device of FIGS. 2a through 2e, however, the inner screw of the variable tension post fixation device of FIGS. 2f through 2g has a fenestrated end. In one embodiment, suture tails 1 and 2 are fed through the openings in the fenestrated end and tied to each other, as are suture tails 3 and 4 (FIG. 2f). In one embodiment, a pronged driver is used to engage the fenestrations and advance the inner screw into the outer sleeve to achieve the desired tension on the sutures (FIG. 2g).

Figure 3A:
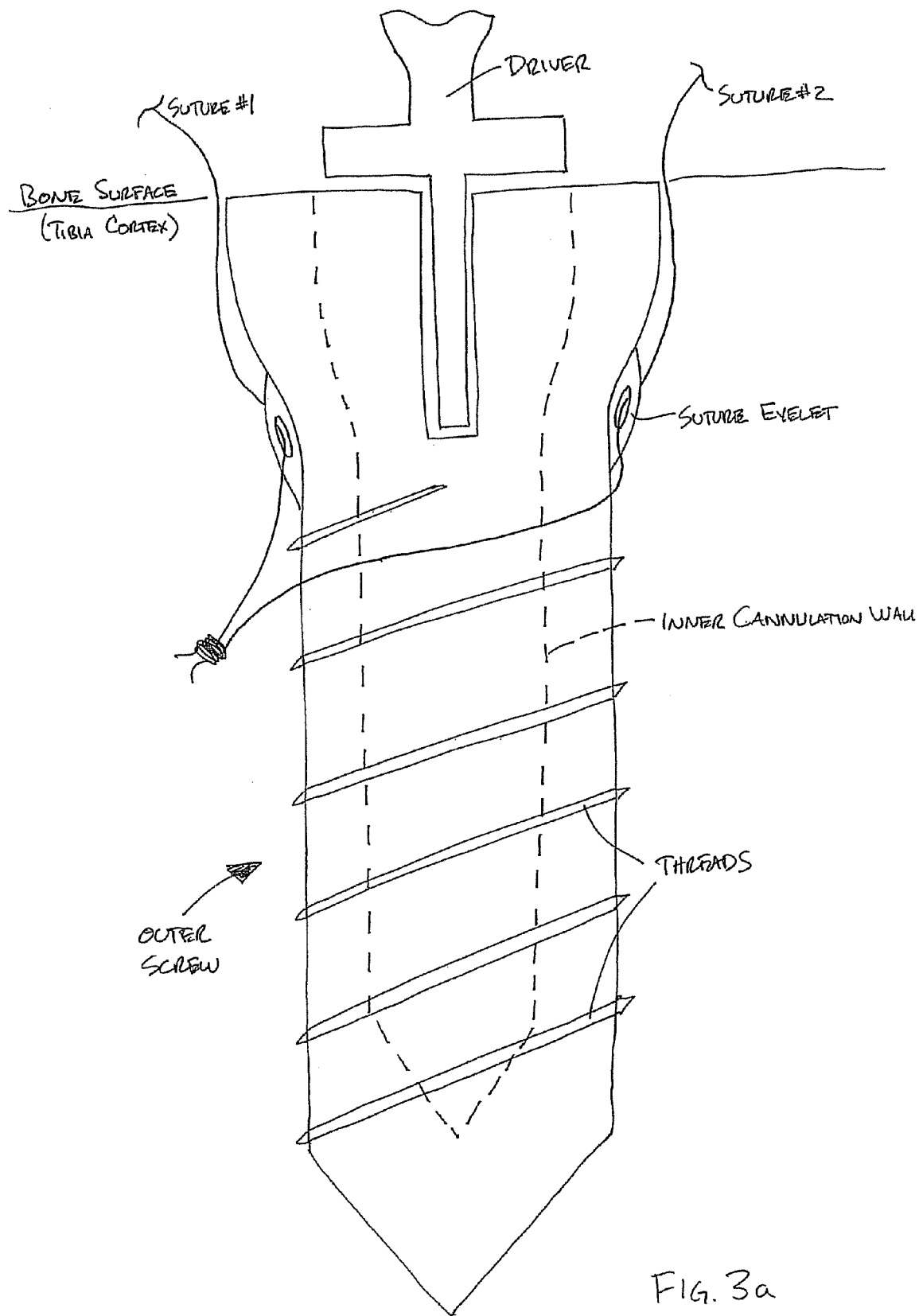
FIGS. 3a through 3h illustrate an embodiment of a variable tension post fixation device.

FIGS. 3a through 3h illustrate another embodiment of a variable tension post fixation device. In one embodiment, as outlined above, a drill is used to create a pilot hole in the tibia distal to the most distal exiting tibial ACL bundle (see FIG. 5). The variable tension post fixation device of FIGS. 3a through 3h includes an outer screw and an inner screw. In one embodiment, the outer screw is a fully threaded headed screw that is inserted flush to the cortex of the tibial bone (FIG. 3a). In one embodiment, the pilot hole is cored out to accommodate the head of the outer screw.

Figure 3B:
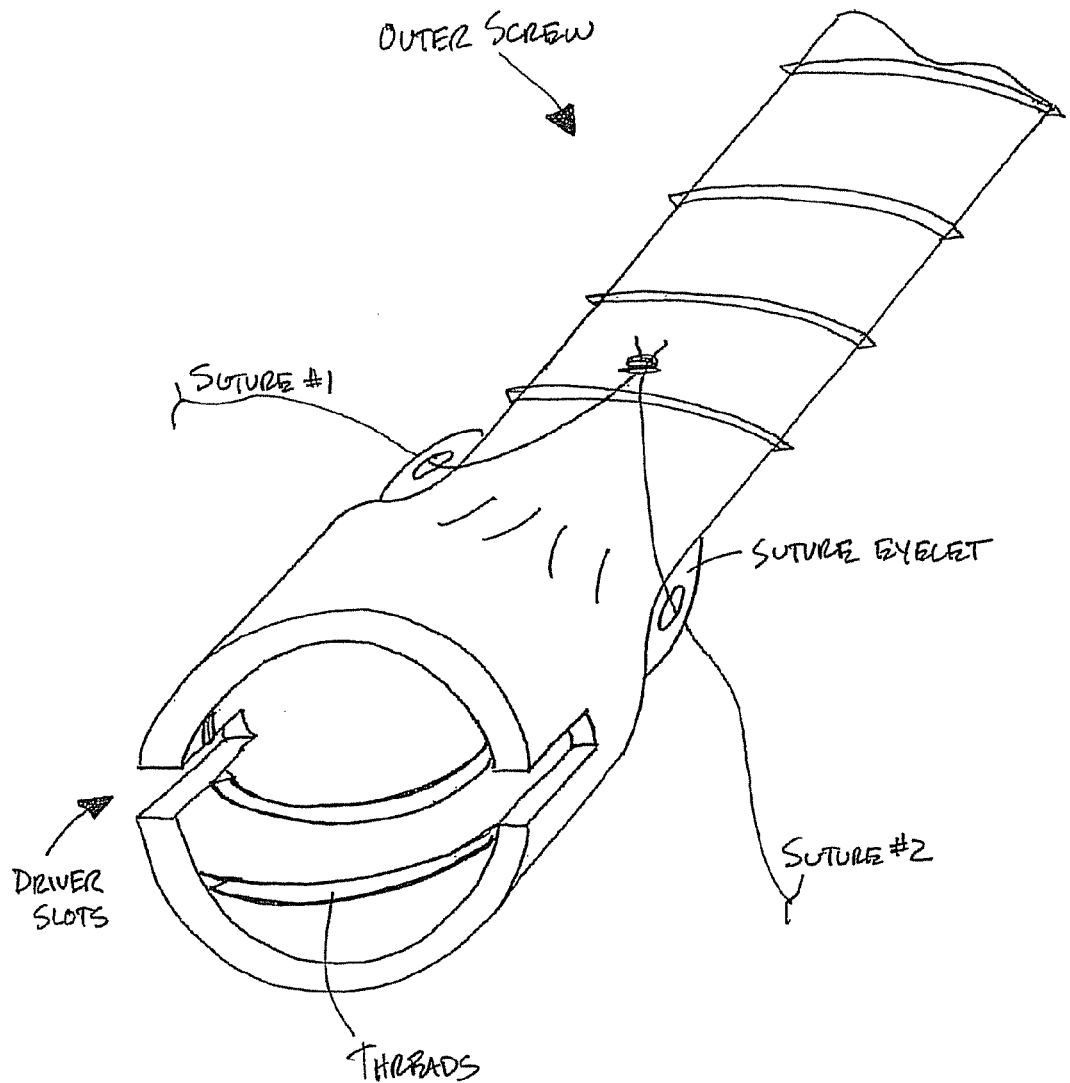

In one embodiment, the outer screw is incompletely cannulated and includes side channels that are cut partially along the sides to receive mating expansion keys or tabs of a cylindrical driver (FIGS. 3a, 3b). In one embodiment, external suture eyelets are provided beneath the head of the outer screw such that before completely sinking the outer screw head flush with the cortex of the tibial bone, suture tails 1 and 2 are fed through the external eyelets and tied to each other (FIG. 3a, 3b). The outer screw head is then sunk flush with the cortex of the tibial bone whereby suture tails 1 and 2 are tensioned (FIG. 3d).

Figure 3C:
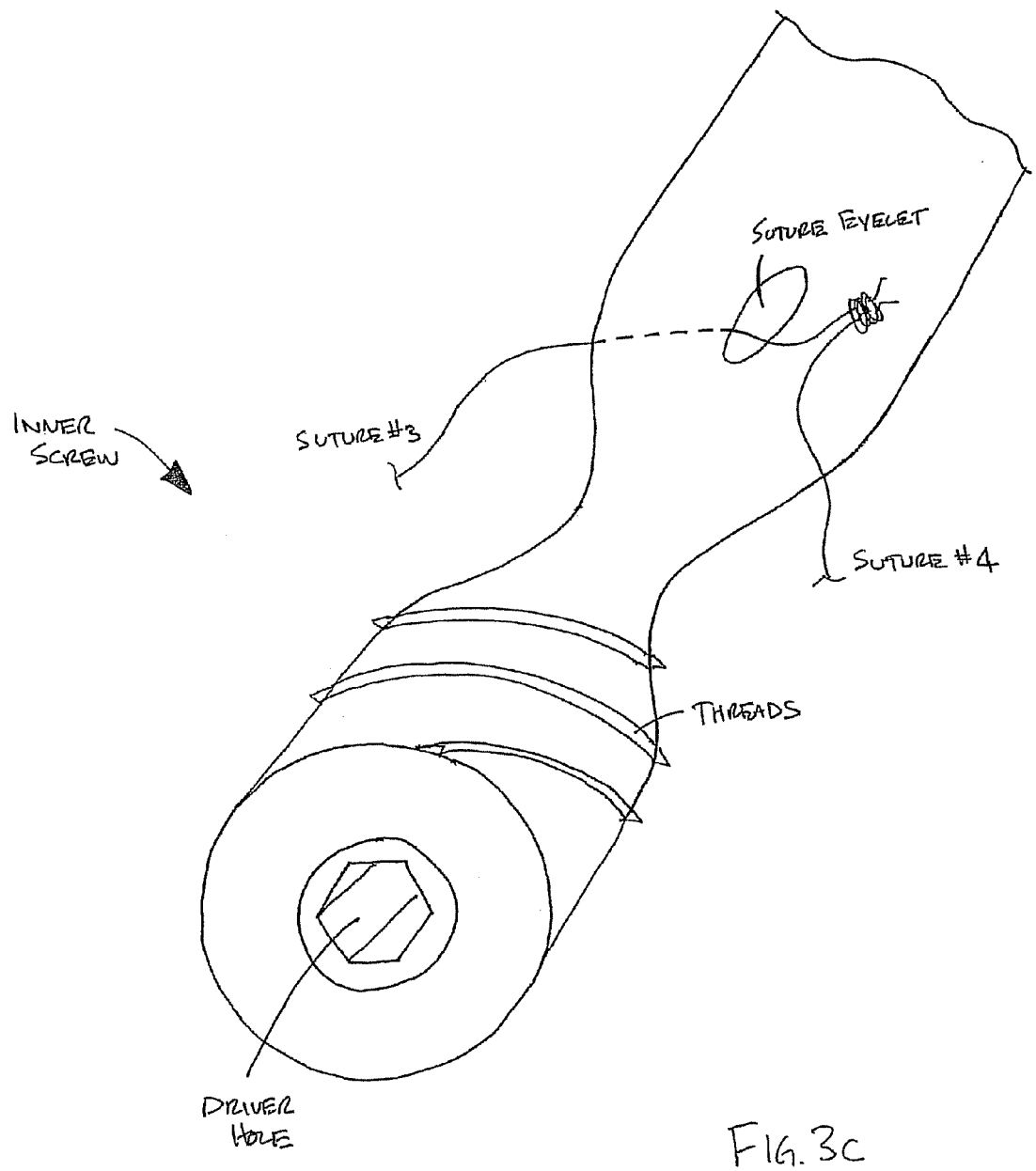
Figure 3D:
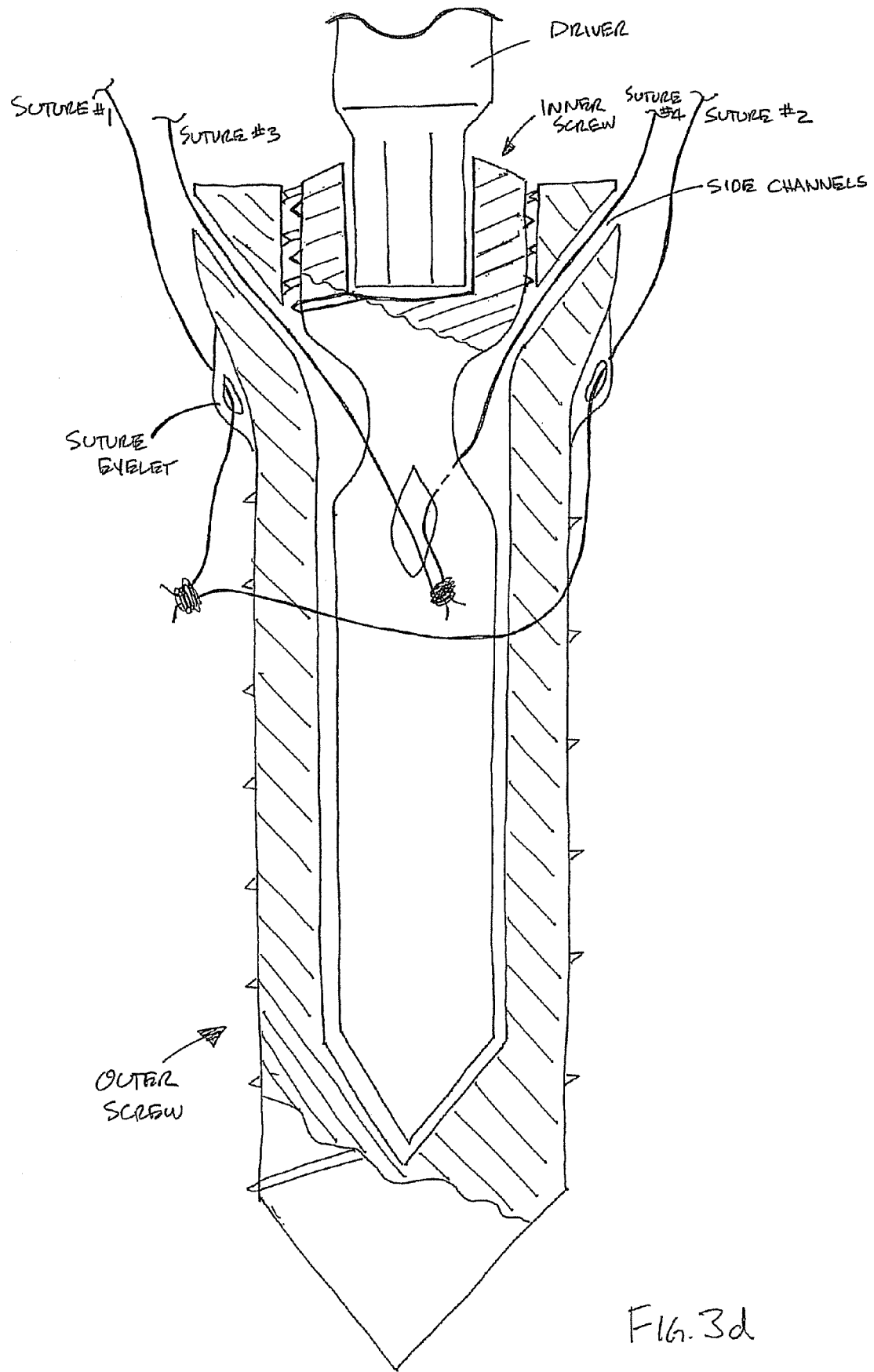

In one embodiment, the shaft of the inner screw includes a central hole through which suture tails 3 and 4 are fed and then tied to each other (FIG. 3c, 3d). In one embodiment, the inner screw includes a partially threaded portion that is thread into the outer screw whereby the inner screw is pressed into the outer screw until the threads of the inner screw engage the locking threads of the outer screw cannulation (FIG. 3c, 3d). As such, the inner screw is rotated until the desired tension is achieved on the suture tails 3 and 4. With the inner screw thread into the outer screw, the inner screw and the outer screw are now a single construct. If further tension on the sutures is desired, the driver may be introduced into the inner screw and the whole construct can be further rotated and advanced.

In one embodiment, the shaft of the inner screw narrows under the head to accommodate the suture tails 3 and 4 as the inner screw is rotated within the outer screw. In addition, in one embodiment, to avoid entanglement of suture tails 3 and 4 in the locking threads between the inner screw and the outer screw, the sutures are fed through side channels provided in the outer screw before the locking threads are engaged.

Figure 3E:
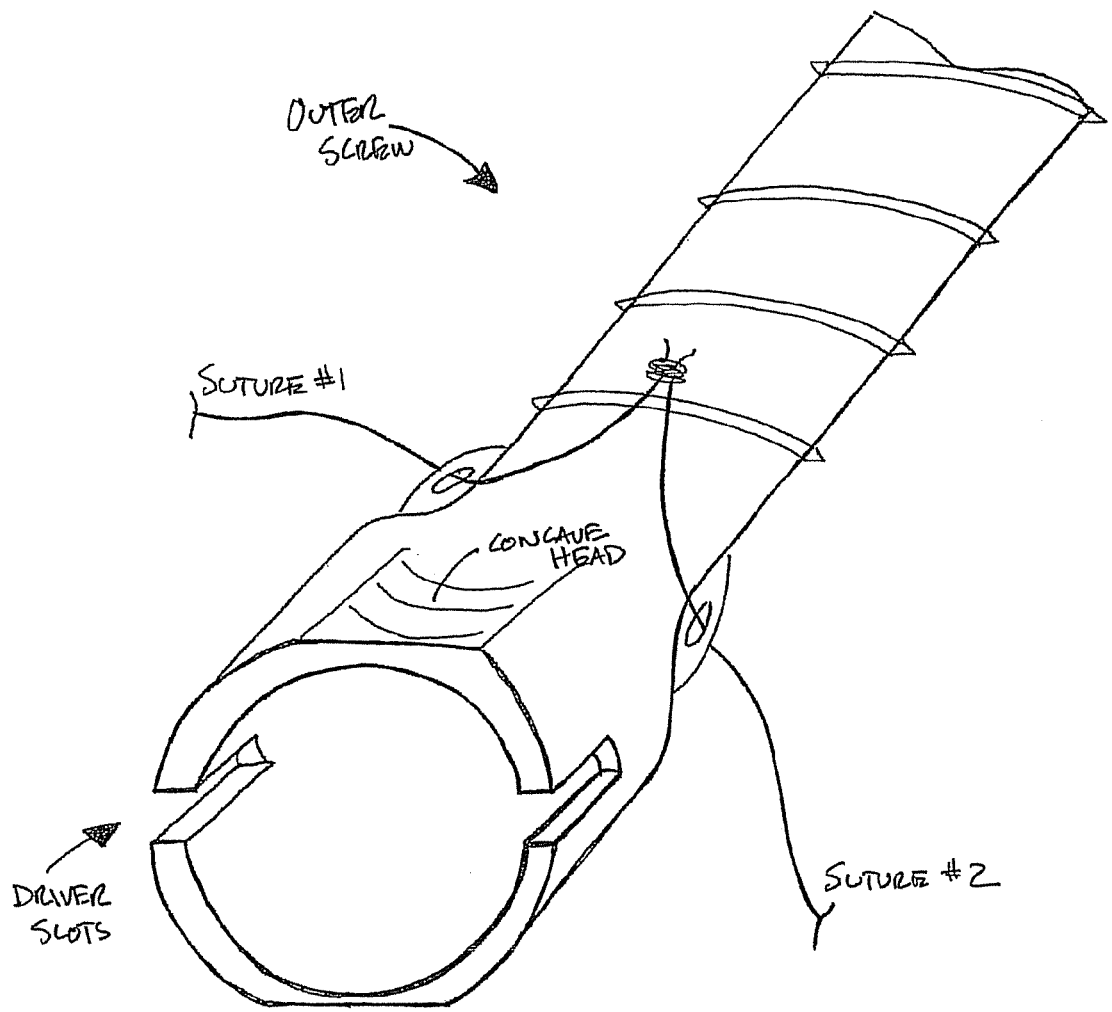
Figure 3F:
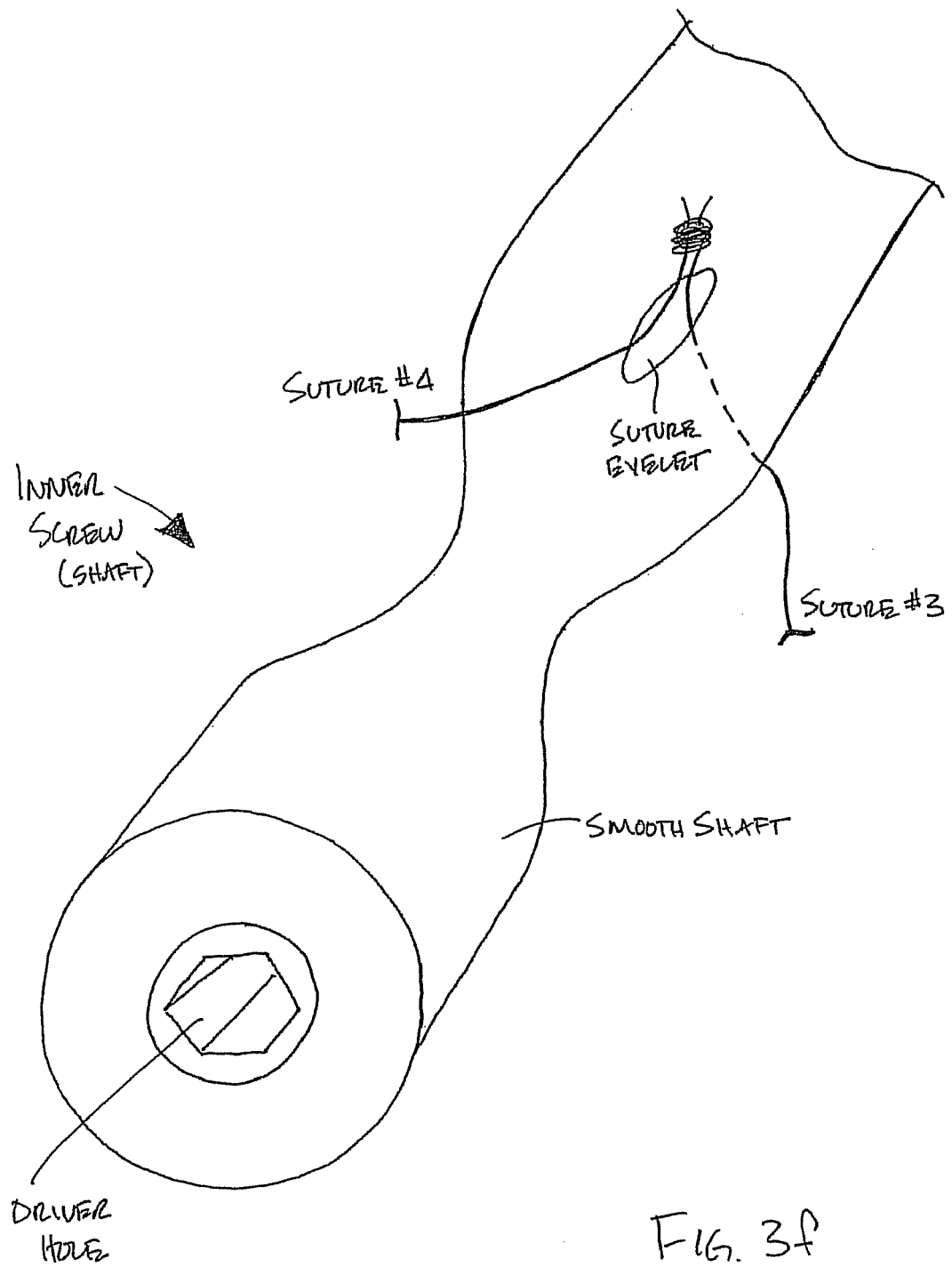
Figure 3G:
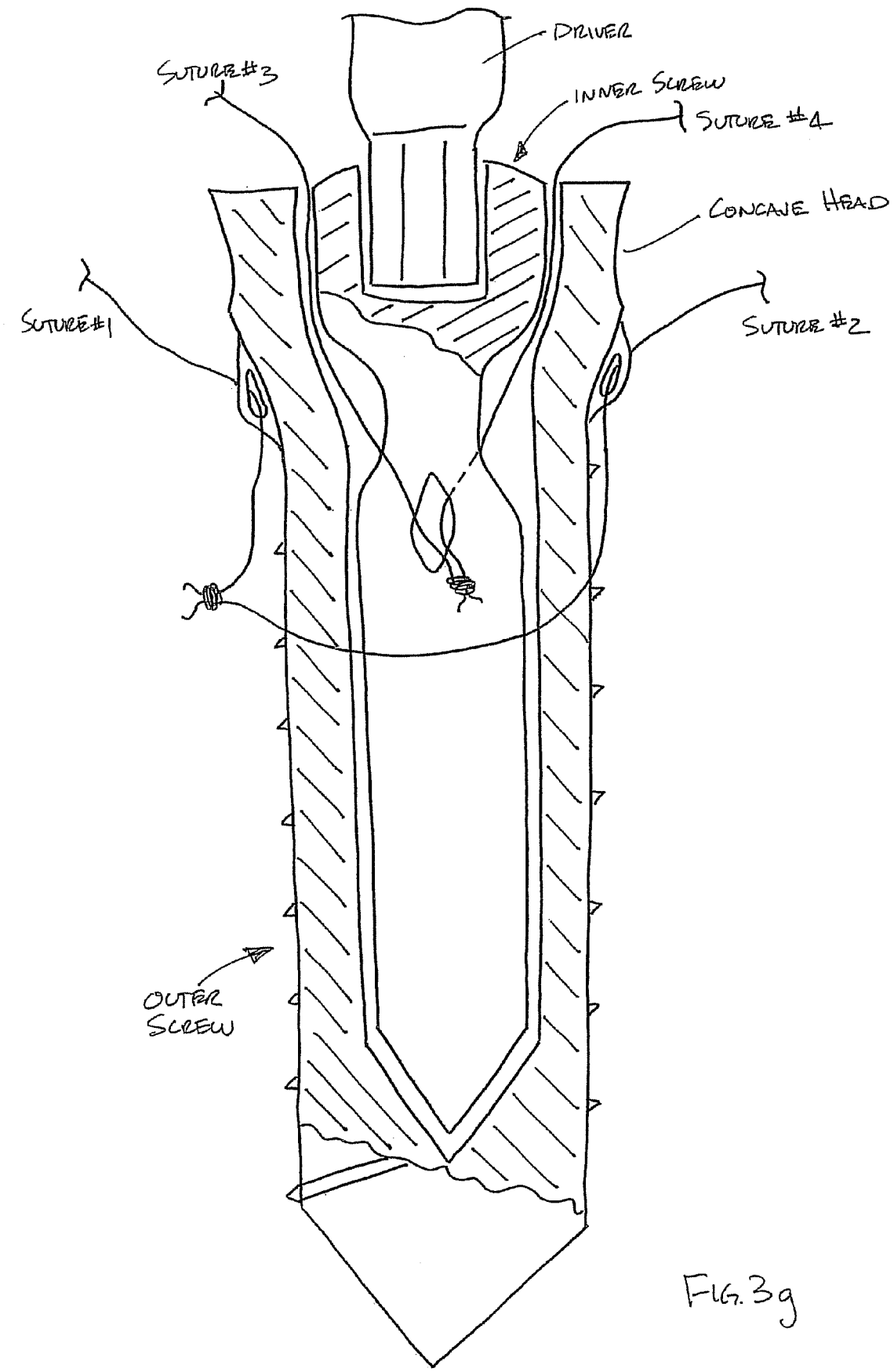

The variable tension post fixation device of FIGS. 3e through 3h is similar to the variable tension post fixation device of FIGS. 3a through 3d, however, the outer screw of the variable tension post fixation device of FIGS. 3e through 3h has a concave outer portion (FIGS. 3e, 3g). In addition, the inner screw is free of threads (FIGS. 3f, 3g).

In one embodiment, suture tails 1 and 2 are fed through the suture eyelets provided on the outer screw, and the outer screw is thread into the pilot hole as described above (FIG. 3g). In addition, sutures tails 3 and 4 are fed through the central hole of the shaft of the inner screw and then tied to each other. Thereafter, the inner screw is press fit into the outer screw to tension suture tails 3 and 4 (FIG. 3g).

Figure 3H:
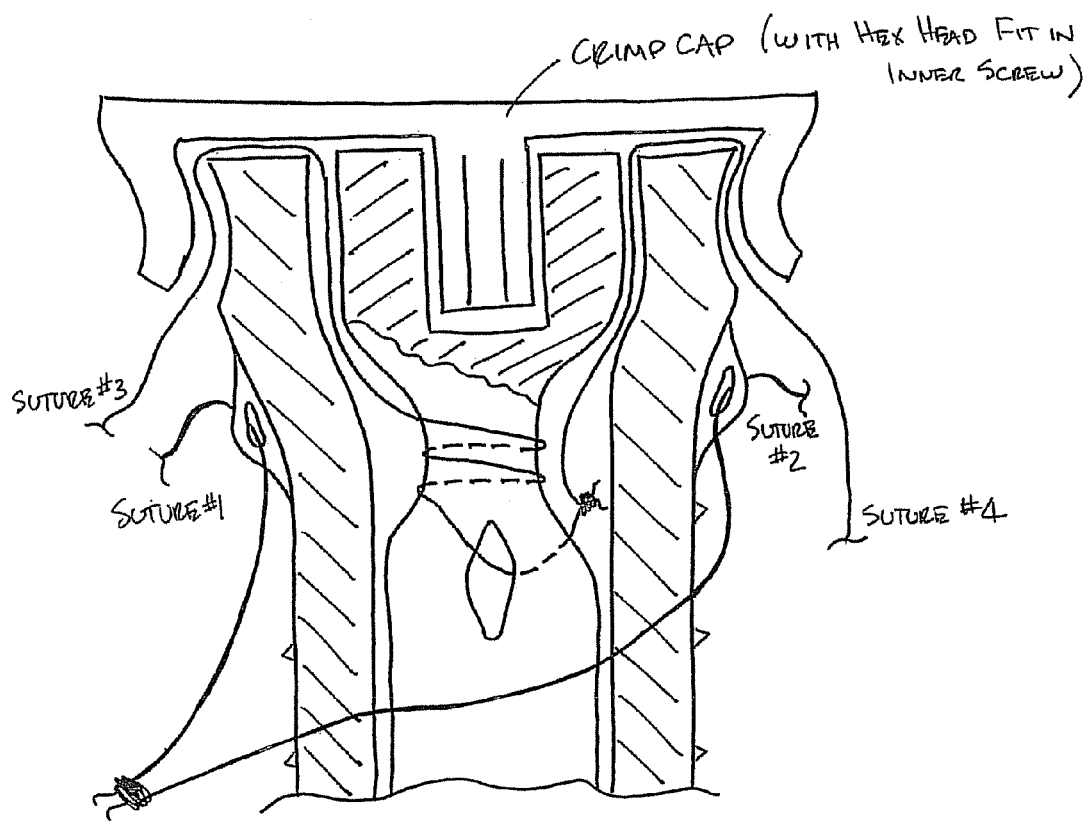

In one embodiment, prior to tensioning suture tails 3 and 4, a cap that engages the inner screw with its own hex head is placed on the inner screw. As such, the cap and the inner screw are rotated to achieve the desired tension on sutures 3 and 4. Once the desired tension is achieved, the inner screw is press fit into the outer screw and the cap is crimped onto the outer screw. The outer screw, the inner screw, and the cap are now a single unit (FIG. 3h). Thus, further tensioning can be achieved with the crimping device on the cap by rotating the entire construct.

Figure 4A:
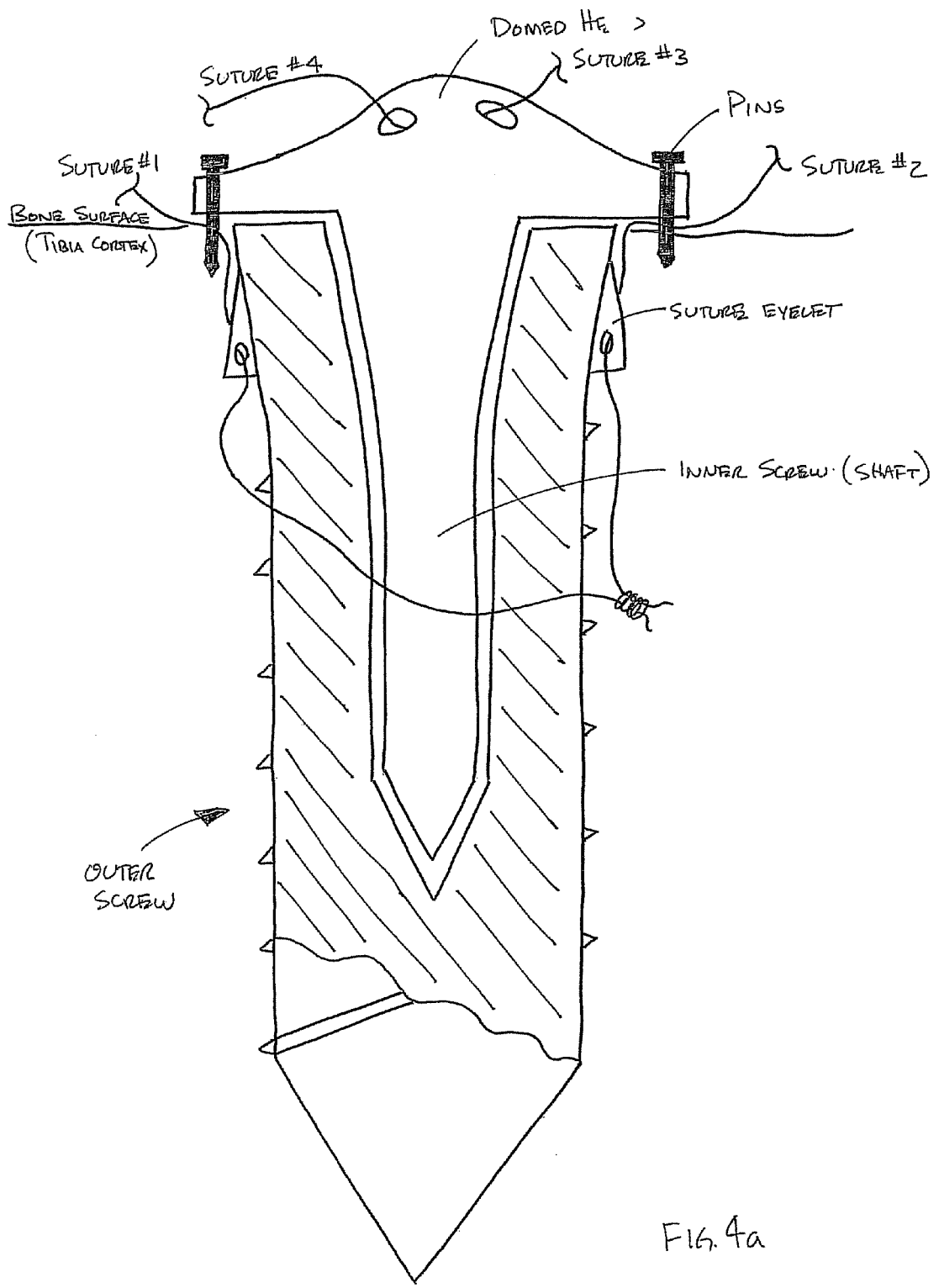
FIGS. 4a through 4b illustrate an embodiment of a variable tension post fixation device.
Figure 4B:
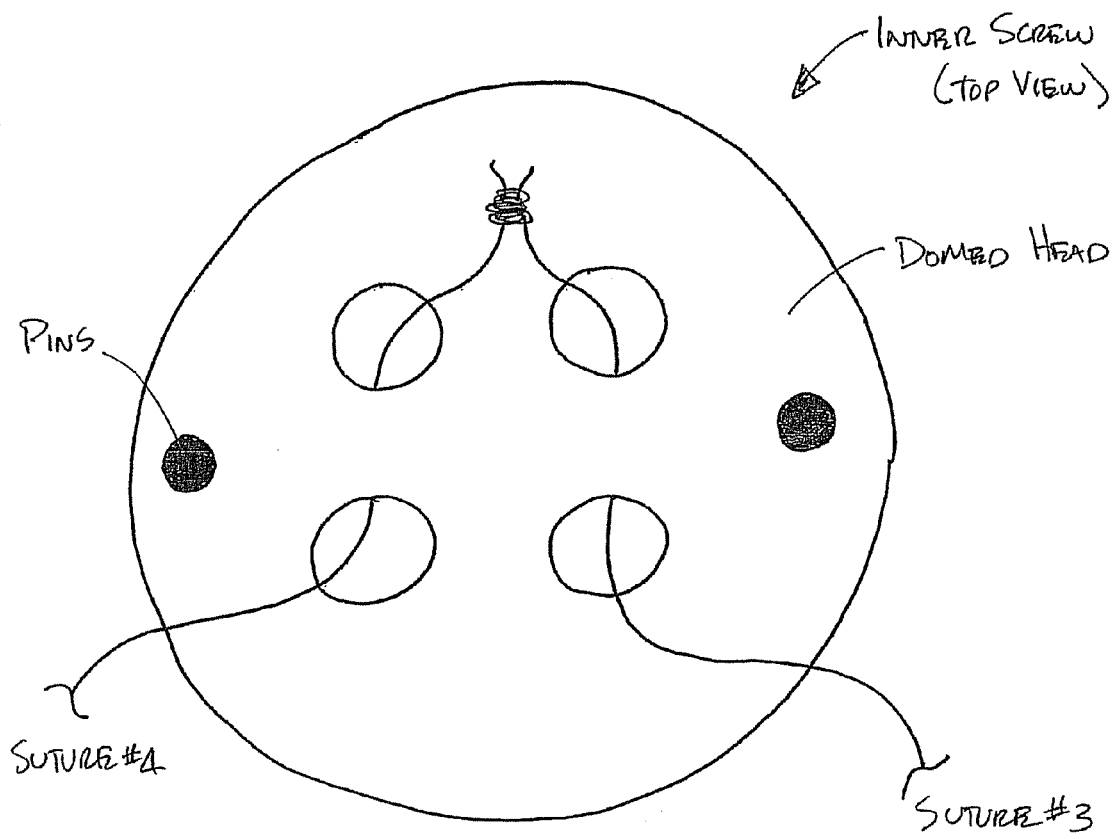

FIGS. 4a through 4b illustrate another embodiment of a variable tension post fixation device. In one embodiment, as outlined above, a drill is used to create a pilot hole in the tibia distal to the most distal exiting tibial ACL bundle (see FIG. 5). The variable tension post fixation device of FIGS. 4a through 4b includes an outer screw and an inner screw. In one embodiment, the outer screw is a fully threaded headed screw that is inserted flush to the cortex of the tibial bone (FIG. 4a).

In one embodiment, the outer screw is incompletely cannulated and includes side channels that are cut partially along the sides to receive mating expansion keys or tabs of a cylindrical driver, as described above. In one embodiment, external suture eyelets are provided beneath the head of the outer screw such that before completely sinking the outer screw head flush with the cortex of the tibial bone, suture tails 1 and 2 are fed through the external eyelets and tied to each other (FIG. 4a). The outer screw head is then sunk flush with the cortex of the tibial bone whereby suture tails 1 and 2 are fully tensioned (FIG. 4a).

In one embodiment, the inner screw is free of threads and includes a shaft that fits inside the outer screw (FIG. 4a). In one embodiment, the head of the inner screw is domed and includes four holes through which suture tails 3 and 4 are fed and then tied together (FIGS. 4a, 4b). In one embodiment, the head of the inner screw also includes two additional holes positioned peripherally which are used to rotate the inner screw and develop the desired tension on suture tails 3 and 4. In one embodiment, once the desired tension is achieved, two anchoring screws or pins are inserted through the additional holes in the head of the inner screw and into the tibia (FIG. 4a). The anchoring screws or pins fix the head of the inner screw to the bone and secure the tension on suture tails 3 and 4.

The embodiments of a variable tension post fixation device described herein provide orthopaedic surgeons with the option of using a single tibial post for fixation and the ability to provide variable tension independently to more than one suture stand.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A variable tension post fixation device, comprising:
    an outer body including a shaft, a tip, and a central core, the outer body configured to be inserted into a pilot hole in a bone; and
    an inner body including a shaft, a tip, and a head, the inner body configured to be advanced within the central core of the outer body,
    wherein the central core of the outer body includes a closed end configured to receive a driver,
    wherein the shaft of the inner body includes a radially extended suture hole, and the head of the inner body includes at least one axially extended suture hole.

2. The device of claim 1, wherein the central core of the outer body includes a series of non-threaded concentric bores configured to separately and distinctly receive the driver and the inner body.

3. The device of claim 2, wherein the tip of the inner body is configured to be rotatably locked within a locking channel of the series of non-threaded concentric bores.

4. The device of claim 1, wherein the head of the inner body includes locking pin slots configured to cooperate with locking pin slots of the outer body to prevent the inner body from rotating relative to the outer body in a locked position.

5. The device of claim 1, wherein the at least one axially extended suture hole comprises at least one pair of axially oriented suture holes.

6. The device of claim 1, wherein the outer body is a threaded, headless screw.

7. The device of claim 1, wherein the inner body is advanced to a locked position within the central core of the outer body.

8. The device of claim 1, wherein the head of the inner body is configured to receive a driver.

9. The device of claim 1, wherein a diameter of the tip of the inner body and a diameter of the head of the inner body are each greater than a diameter of the shaft of the inner body.

10. A device for variable tension suture fixation, comprising:
    an outer body configured for insertion into bone and comprising a threaded shaft, a conical tip extending from a first end, and an incompletely cannulated core extending open to a second end; and
    an inner body configured for rotatable insertion into the incompletely cannulated core and comprising a key shaft, a key tip provided at a first end, and a key head provided at a second end, the key shaft including a radially oriented suture hole, and the key head including at least one axially oriented suture hole, wherein a closed end of the incompletely cannulated core includes a driver hole configured to receive a driver.

11. The device of claim 10, wherein the at least one axially oriented suture hole includes at least two axially extended suture holes.

12. The device of claim 10, wherein an outer diameter of the key head is greater than an outer diameter of the key shaft.

13. The device of claim 10, wherein an outer diameter of the key tip is greater than an outer diameter of the key shaft.

14. The device of claim 10, wherein the key head is configured to receive a driver.

15. The device of claim 10, wherein the incompletely cannulated core comprises a series of non-threaded concentric bores open to the second end.

16. The device of claim 15, wherein the inner body comprises a non-threaded inner key configured to be rotatably inserted in and lockingly engaged with the series of non-threaded concentric bores.

17. A device for variable tension suture fixation, comprising:

an outer screw including an externally threaded shaft, a conical tip at a first end, and a series of non-threaded concentric bores open to a second end; and a non-threaded inner key including a key shaft, a key tip at a first end, a key head at a second end, a suture hole in the key shaft, and at least one suture hole in the key head, wherein the outer screw is configured to be inserted into bone and has a driver hole at a closed end of the series of non-threaded concentric bores, and wherein the non-threaded inner key is configured to be rotatably inserted in and lockingly engaged with the series of non-threaded concentric bores of the outer screw.

18. The device of claim 17, wherein the suture hole in the key shaft comprises a radially oriented suture hole, and the at least one suture hole in the key head comprises at least one pair of axially oriented suture holes.

* * * * *